(12) United States Patent
Farmer

(10) Patent No.: US 6,723,326 B1
(45) Date of Patent: *Apr. 20, 2004

(54) TOPICAL COMPOSITIONS CONTAINING PROBIOTIC BACILLUS BACTERIA, SPORES, AND EXTRACELLULAR PRODUCTS AND USES THEREOF

(75) Inventor: Sean Farmer, San Diego, CA (US)

(73) Assignee: Ganeden Biotech, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/620,622

(22) Filed: Jul. 20, 2000

Related U.S. Application Data

(60) Division of application No. 09/383,975, filed on Aug. 26, 1999, now Pat. No. 6,645,506, which is a continuation-in-part of application No. PCT/US98/07307, filed on Apr. 10, 1998.

(60) Provisional application No. 60/044,643, filed on Apr. 18, 1997.

(51) Int. Cl.[7] ........................ A61K 39/108; A61K 6/00; A61K 35/12; A01N 63/00; A01N 25/34

(52) U.S. Cl. ............................... 424/246.1; 424/93.46; 424/260.1; 424/522; 424/401; 424/402; 424/404; 424/434; 435/252.3

(58) Field of Search .................... 424/246.1, 260.1, 424/431, 404, 93.46, 401, 402, 409, 115, 522; 435/252.3

(56) References Cited

U.S. PATENT DOCUMENTS

| | | | |
|---|---|---|---|
| 4,110,477 A | | 8/1978 | Naruse et al. |
| 4,323,651 A | * | 4/1982 | Long et al. |
| 5,079,164 A | | 1/1992 | Kirkovits et al. |
| 5,176,911 A | | 1/1993 | Tosi et al. |
| 5,439,678 A | | 8/1995 | Dobrogosz et al. |
| 5,849,289 A | * | 12/1998 | Dobrogosz et al. ...... 424/93.45 |
| 6,461,607 B1 | * | 10/2002 | Farmer .................... 424/93.45 |
| 6,531,126 B2 | * | 3/2003 | Farmer ........................ 424/115 |
| 6,645,506 B1 | * | 11/2003 | Farmer .................... 424/260.1 |
| 2001/0033838 A1 | * | 10/2001 | Farmer ........................ 424/115 |
| 2003/0003107 A1 | * | 1/2003 | Farmer .................... 424/184.1 |
| 2003/0031659 A1 | * | 2/2003 | Farmer .................... 424/93.45 |

FOREIGN PATENT DOCUMENTS

| | | |
|---|---|---|
| WO | WO 93/14187 | 7/1993 |
| WO | WO 94/11492 | 5/1994 |
| WO | WO 97/02846 | 1/1997 |
| WO | WO 98/47374 | 10/1998 |
| WO | WO 00/07606 | 2/2000 |
| WO | WO 00/10582 | 3/2000 |
| WO | WO 00/61201 | 10/2000 |

OTHER PUBLICATIONS

Sussman, et al., 1986. Clinical manifestations and therapy of *Lactobacillus endocarditis*: report of a case and review of the literature. *Rev Infect. Dis. 8:* 771–776.

Hata, et al., 1988. Meningitis caused by Bifidobacterium in an infant. *Pediatr. Infect. Dis. 7:* 669–671.

Reid, et al, 1990. Is there a role for lactobacilli in prevention of urogenital and intestinal infections? *Clin. Microbiol. Rev. 3:* 335–344.

Gibson, et al., 1995. Selective stimulation of bifidobacteria in the human colon by oligofructose and inulin. *Gastroenterology 106:* 975–982.

Saavedra, 1994. Feeding of *Bifidobacterium bifidum* and *Streptococcus thermophilus* to infants in hospital for prevention of diarrhoea and shedding of rotavirus. *Lancet 344:* 1046–109.

Mitchell, 1998. Rearming in the fight against bacteria. *Lancet 352:* 462–463.

Shannon, 1998. Multiple–antibiotic–resistant salmonella. *Lancet 352:* 490–491.

Thomason, et al, 1991. Bacterial vaginosis: current review with indications for asymptomatic therapy. *Am. J. Obstet Gynecol. 165:* 1210–1217.

Marsh, 1993. Antimicrobial strategies in the prevention of dental caries. *Caries Res. 27:* 72–76.

Hill & Embil, 1986. Vaginitis: current microbiologic and clinical concepts. *Can. Med. Assoc. J. 134:* 321–331.

Fuller, R., 1989. Probiotics in man and animals. *J. Appl. Bacteriol. 66:* 365–378.

Nakamura, et al., 1988. Taxonomic study for *Bacillus coagulans* Hammer 1915. *J. Systematic Bacterio. 38:* 63–73.

(List continued on next page.)

Primary Examiner—N. M. Minnifield
(74) Attorney, Agent, or Firm—Mintz Levin Cohn Ferris Glovsky and Popeo, P.C.

(57) ABSTRACT

The present invention discloses compositions derived from an isolated Bacillus species, spores, or an extracellular product of *Bacillus coagulans* comprising a supernatant or filtrate of a culture of said *Bacillus coagulans* strain, suitable for topical application to the skin or mucosal membranes of a mammal, which are utilized to inhibit the growth of bacterium, yeast, fungi, virus, and combinations thereof. The present invention also discloses methods of treatment and therapeutic systems for inhibiting the growth of bacterium, yeast, fungi, virus, and combinations thereof, by topical application of therapeutic compositions which are comprised, in part, of isolated Bacillus species, spores, or an extracellular product of *Bacillus coagulans* comprising a supernatant or filtrate of a culture of said *Bacillus coagulans* strain. In addition, the present invention also discloses compositions, methods of treatment, and therapeutic systems for inhibiting the growth of bacterium, yeast, fungi, virus, and combinations thereof, comprising an extracellular product of *Pseudomonas lindbergii* comprising a supernatant or filtrate of a culture of said *Pseudomonas lindbergii* strain.

32 Claims, 10 Drawing Sheets

OTHER PUBLICATIONS

Winberg, et al., 1993. Pathogenesis of urinary tract infection–experimental studies of vaginal resistance to colonization. *Ped. Nephrol. 7:* 509–514.

Zemtsov et al., "Moisturizing and cosmetic properties of emu oil: A pilot double blind study", Australasian J. Dermatol. 37:159–162, 1996.

Hodges et al., "Potential biocontrol of sclerotina homeocarpa and bipolaris sorokiniana on the phylloplane of Poa pratensis with strains of Pseudomonas sp.", Plant Path., 43:500–506, 1994.

PCT International Search Report.

* cited by examiner

| Bacillus coagulans Metabolic Activity | Characteristic Response |
|---|---|
| Catalase production | Yes |
| Acid from D-Glucose | Yes |
| Acid from l-Arabinose | Variable |
| Acid from D-Xylose | Variable |
| Acid from D-Mannitol | Variable |
| Gas from Glucose | Yes |
| Hydrolysis of Gelatin | No |
| Hydrolysis of Starch | Yes |
| Utilization of Citrate | Variable |
| Utilization of Propionate | No |
| Degradation of Tyrosine | No |
| Degradation of Phenylalanine | No |
| Nitrate Reduced to Nitrite | Variable |
| Allatoin or Urate Required | No |

Fig. 1

| Infecting Microbe | Condition |
|---|---|
| Trichophyton species | |
| T. mentagrophytes | tinea pedis, athlete's foot |
| T. interdigitale | tinea pedis, athlete's foot |
| T. mentagrophytes | tinea versicolor, ring worm |
| T. mentagrophytes | tinea barbae, face/neck inflammation |
| T. rubrum | dermatophytosis |
| T. yaoundei | ring worm on scalp |
| Candida species | |
| C. albicans | systemic candidaiasis |
| C. albicans | chronic mucocutaneous candidaiasis, myositis and thymoma |
| C. albicans | yeast and mycelial phase infection |
| C. albicans | oral thrush |
| C. tropicalis | cervical yeast infection |
| Pseudomonas aeruginosa | opportunistic skin infections, urinary tract infections, post surgical infections |
| Staphylococcus aureus | opportunistic skin infections, boils, abscess, wound infections, dermatitis |
| Staphylococcus epidermidis | opportunistic skin infections |
| Streptococcus pyogenes | opportunistic skin infections, impetigo, erysipelas |
| Streptococcus spp. | opportunistic skin infections, wound infections |
| Gardnerella vaginalis | bacterial vaginosis |
| Propionibacterium acnes | acne |
| Clostridium perfingens | open-wound infections |
| Herpes Simplex Virus I or II | cold sores, genital herpes lesions |

Fig. 2

| Mycotic Pathogen | Associated Disease | Inhibition Results |
|---|---|---|
| T. mentagrophytes (ATCC No. 4808) | Tinea pedis (Athlete's Foot) | Excellent |
| T. interdigitabe (ATCC No. 9129) | Tinea pedis (Athlete's Foot) | Excellent |
| T. mentagrophytes (ATCC No. 36107) | Tinea versicolor (Ring Worm) | Excellent |
| T. menagrophytes (ATCC No. 8125) | Tinea barbae (Face & Neck Inflammation) | Good |
| T. mentagrophytes (ATCC No. 9533) | Tinea pedis (Athlete's Foot) | Excellent |
| T. mentagrophytes (ATCC No. 28187) | Tinea pedis (Athlete's Foot) | Excellent |
| T. rubrum (ATCC No. 18753) | Mild Dermatophytosis | Good |
| T. yaoundei (ATCC No. 13947) | Ring Worm, Scalp | Good |

Fig. 3

| Species | Pathology | Inhibition Results |
|---|---|---|
| Candida abbicans (ATCC No. 26555) | Chronic Mucocutaneous, Candidiasis, Mytositis and Thymoma | Excellent |
| C. albicans (ATCC No. 44203) | Systemic Candidiasis | Excellent |
| C. albicans (ATCC No. 44807) | Yeast and Mycelial Phase | Excellent |
| C. tropicauis (ATCC No. 62377) | Cervical Yeast Infections | Excellent |

Fig. 4

| Organism | Fluconazole µg/ml | Ganeden supernatant: dilution showing 80% inhibition |
|---|---|---|
| C. albicans | .5 | 1:4 |
| C. glabraia | 8 | Resistant |
| C. parapsilosis | 2 | 1:16 |
| C. krusui | 32 | Resistant |
| T. rubrum | 1.0 | 1:512 |
| T. meniagrophytes | 8.0 | 1:32 |
| A. flavus | >64 | Resistant |
| A. fumigatus | >64 | Resistant |
| Acremonium | >64 | 1:2 |
| Scopulariopsis | .5 | Undiluted |

TOPICAL COMPOSITIONS CONTAINING PROBIOTIC BACILLUS BACTERIA, SPORES, AND EXTRACELLULAR PRODUCTS AND USES THEREOF

RELATED APPLICATIONS

The present application is a divisional application of patent application Ser. No. 09/383,975, filed on Aug. 26, 1999 now U.S. Pat. No. 6,645,506, which is a continuation-in-part (CIP) of, and claims priority to PCT Patent Ser. No. PCT/US98/07307 entitled: "TOPICAL USE OF PROBIOTIC BACILLUS SPORES TO PREVENT OR CONTROL MICROBIAL INFECTIONS", filed Apr. 10, 1998 and U.S. Provisional Patent Application Ser. No. 60/044,643, entitled: "TOPICAL USE OF PROBIOTIC BACILLUS SPORES TO PREVENT OR CONTROL MICROBIAL INFECTIONS", filed Apr. 18, 1997.

FIELD OF THE INVENTION

The present invention relates to the utilization of a probiotic, viable Bacillus bacteria, spores, and extracellular supernatant products in therapeutic compositions as a topical agent. More specifically, the present invention relates to the use of therapeutic compositions derived from *Bacillus coagulans* for the prevention and/or control of infections caused by bacterium, fungi, yeast, and virus, and combinations thereof. The present invention also relates to the use of extracellular product of *Pseudomonas lindbergii* comprising a supernatant or filtrate of a culture of said *Pseudomonas lindbergii* strain for the prevention and/or control of infections caused by bacterium, fungi, yeast, and virus, and combinations thereof.

BACKGROUND OF THE INVENTION

1. Probiotic Microorganisms

Probiotic microorganisms are those which confer a benefit when grow in a particular environment, often by inhibiting the growth of other biological organisms in the same environment. Examples of probiotic organisms include bacteria and bacteriophages which possess the ability to grow within the gastrointestinal tract, at least temporarily, to displace or destroy pathogenic organisms, as well as providing other benefits to the host. See e.g., Salminen et al, 1996. *Antonie Van Leeuwenhoek* 70: 347–358; Elmer et al, 1996. *JAMA* 275: 870–876; Rafter, 1995. *Scand. J. Gastroenterol.* 30: 497–502; Perdigon et al, 1995. *J Dairy Sci.* 78: 1597–1606; Gandi, *Townsend Lett. Doctors & Patients*, pp. 108–110, January 1994; Lidbeck et al, 1992. *Eur. J. Cancer Prev.* 1: 341–353.

The majority of previous studies on probiosis have been observational rather than mechanistic in nature, and thus the processes responsible for many probiotic phenomena have yet to be quantitatively elucidated. Some probiotics are members of the normal colonic microflora and are not viewed as being overtly pathogenic. However, these organisms have occasionally caused infections (e.g., bacteremia) in individuals who are, for example, immunocompromised. See e.g., Sussman, J. et al., 1986. *Rev Infect. Dis.* 8: 771–776; Hata, D. et al., 1988. *Pediatr. Infect. Dis.* 7: 669–671.

For example, the probiotic bacteria found in sour milk, has been utilized since ancient times (i.e., long-before the discovery of bacteria) as a therapeutic treatment for dysentery and related gastrointestinal diseases. More recently, probiotic preparations were systematically evaluated for their effect on health and longevity in the early-1900's (see e.g., Metchinikoff, E., *Prolongation of Life*, Willaim Heinermrann, London 1910), although their utilization has been markedly limited since the advent of antibiotics in the 1950's to treat pathological microbes. See e.g., Winberg, et al, 1993. *Pediatr. Nephrol.* 7: 509–514; Malin et al, *Ann. Nutr. Metab.* 40: 137–145; and U.S. Pat. No. 5,176,911. Similarly, lactic acid-producing bacteria (e.g., Bacillus, Lactobacillus and Streptococcus species) have been utilized as food additives and there have been some claims that they provide nutritional and/or therapeutic value. See e.g., Gorbach, 1990. *Ann. Med.* 22: 37–41; Reid et al, 1990. *Clin. Microbiol. Rev.* 3: 335–344.

The best known probiotics are the lactic acid-producing bacteria (i.e., Lactobacilli) and Bifidobacteria, which are widely utilized in yogurts and other dairy products. These probiotic organisms are non-pathogenic and non-toxigenic, retain viability during storage, and possess the ability to survive passage through the stomach and small intestine. Since probiotics do not permanently colonize the host, they need to be ingested or applied regularly for any health-promoting properties to persist. Commercial probiotic preparations are generally comprised of mixtures of Lactobacilli and Bifidobacteria, although yeast such as Saccharomyces have also been utilized.

2. Gastrointestinal Microflora

Perhaps the best-characterized use of probiotic microorganisms is in the maintenance of gastrointestinal microflora. The gastrointestinal microflora has been shown to play a number of vital roles in maintaining gastrointestinal tract function and overall physiological health. For example, the growth and metabolism of the many individual bacterial species inhabiting the gastrointestinal tract depend primarily upon the substrates available to them, most of which are derived from the diet. See e.g., Gibson G. R. et al., 1995. *Gastroenterology* 106: 975–982; Christl, S. U. et al., 1992. *Gut* 33: 1234–1238. These finding have led to attempts to modify the structure and metabolic activities of the community through diet, primarily with probiotics which are live microbial food supplements.

While the attachment of probiotics to the gastrointestinal epithelium is an important determinant of their ability to modify host immune reactivity, this is not a universal property of Lactobacilli or Bifidobacteria, nor is it essential for successful probiosis. See e.g., Fuller, R., 1989. *J. Appl. Bacteriol.* 66: 365–378. For example, adherence of *Lactobacillus acidophilus* and some Bifidobacteria to human enterocyte-like CACO-2 cells has been demonstrated to prevent binding of enterotoxigenic and enteropathogenic *Escherichia coli*, as well as *Salmonella typhimurium* and *Yersinia pseudotuberculosis*. See e.g., Bernet, M. F. et al, 1994. *Gut* 35: 483–489; Bernet, M. F. et al., 1993. *Appl. Environ. Microbiol.* 59: 4121–4128.

While the gastrointestinal microflora presents a microbial-based barrier to invading organisms, pathogens often become established when the integrity of the microbiota is impaired through stress, illness, antibiotic treatment, changes in diet, or physiological alterations within the gastrointestinal tract. For example, Bifidobacteria are known to be involved in resisting the colonization of pathogens in the large intestine. See e.g., Yamazaki, S. et al, 1982. *Bifidobacteria and Microflora* 1: 55–60. Similarly, the administration of *Bifidobacteria breve* to children with gastroenteritis eradicated the causative pathogenic bacteria (i.e., *Campylobacter jejuni*) from their stools (see e.g., Tojo, M., 1987. *Acta Pediatr. Jpn.* 29: 160–167) and supplementation of infant formula milk with *Bifidobacteria bifidum* and *Streptococcus thermophilus* was found to reduce rotavirus shedding and episodes of diarrhea in children who were hospitalized (see e.g., Saavedra, J. M., 1994. *The Lancet* 344: 1046–109.

In addition, some lactic acid producing bacteria also produce bacteriocins which are inhibitory metabolites which are responsible for the bacteria's anti-microbial effects. See e.g., Klaenhammer, 1993. *FEMS Microbiol. Rev.* 12:39–85; Barefoot et al., 1993. *J. Diary Sci.* 76: 2366–2379. For example, selected Lactobacillus strains which produce antibiotics have been demonstrated as effective for the treatment of infections, sinusitis, hemorrhoids, dental inflammations, and various other inflammatory conditions. See e.g, U.S. Pat. No. 5,439,995. Additionally, *Lactobacillus reuteri* has been shown to produce antibiotics which possess anti-microbial activity against Gram negative and Gram positive bacteria, yeast, and various protozoan. See e.g., U.S. Pat. Nos. 5,413,960 and 5,439,678.

Probiotics have also been shown to possess anti-mutagenic properties. For example, Gram positive and Gram negative bacteria have been demonstrated to bind mutagenic pyrolysates which are produced during cooking at a high temperature. Studies performed with lactic acid-producing bacteria has shown that these bacteria may be either living or dead, due to the fact that the process occurs by adsorption of mutagenic pyrolysates to the carbohydrate polymers present in the bacterial cell wall. See e.g., Zang, X. Bacillus et al., 1990. *J. Dairy Sci.* 73: 2702–2710. Lactobacilli have also been shown to possess the ability to degrade carcinogens (e.g., N-nitrosamines), which may serve an important role if the process is subsequently found to occur at the level of the mucosal surface. See e.g., Rowland, I. R. and Grasso, P., *AppL. Microbiol.* 29: 7–12. Additionally, the co-administration of lactulose and *Bifidobacteria longum* to rats injected with the carcinogen azoxymethane was demonstrated to reduce intestinal aberrant crypt foci, which are generally considered to be pre-neoplastic markers. See e.g., Challa, A. et al., 1997. *Carcinogenesis* 18: 5175–21. Purified cell walls of Bifidobacteria may also possess anti-tumorigenic activities in that the cell wall of *Bifidobacteria infantis* induces the activation of phagocytes to destroy growing tumor cells. See e.g., Sekine, K. et al., 1994. Bifidobacteria and Microflora 13: 65–77. Bifidobacteria probiotics have also been shown to reduce colon carcinogenesis induced by 1,2-dimethylhydrazine in mice when concomitantly administered with fructo-oligosaccharides (FOS; see e.g., Koo and Rao, 1991. *Nutrit. Rev.* 51: 137–146), as well as inhibiting liver and mammary tumors in rats (see e.g., Reddy and Rivenson, 1993. *Cancer Res.* 53: 3914–3918).

It has also been demonstrated that the microbiota of the gastrointestinal tract affects both mucosal and systemic immunity within the host. See e.g., Famularo, G. et al., Stimulation of Immunity by Probiotics. In: *Probiotics: Therapeutic and Other Beneficial Effects*. pg. 133–161. (Fuller, R., ed. Chapman and Hall, 1997). The intestinal epithelial cells, blood leukocytes, B- and T-lymphocytes, and accessory cells of the immune system have all been implicated in the aforementioned immunity. See e.g., Schiffrin, E. J. et al., 1997. *Am J. Clin. Nutr.* 66: 5–20S. Other bacterial metabolic products which possess immunomodulatory properties include: endotoxic lipopolysaccharide, peptidoglycans, and lipoteichoic acids. See e.g., Standiford, T. K., 1994. *Infect. Linmun.* 62: 119–125. Accordingly, probiotic organisms are thought to interact with the immune system at many levels including, but not limited to: cytokine production, mononuclear cell proliferation, macrophage phagocytosis and killing, modulation of autoimmunity, immunity to bacterial and protozoan pathogens, and the like. See e.g., Matsumara, K. et al., 1992. *Animal Sci. Technol.* (Jpn) 63: 1157–1159; Solis-Pereyra, B. and Lemmonier, D., 1993. *Nutr. Res.* 13: 1127–1140. Lactobacillus strains have also been found to markedly effect changes in inflammatory and immunological responses including, but not limited to, a reduction in colonic inflammatory infiltration without eliciting a similar reduction in the numbers of B- and T-lymphocytes. See e.g., De Simone, C. et al., 1992. *Immunopharmacol. Immunotoxicol.* 14: 331–340.

3. Physiological Effects of Antibiotic Administration

Antibiotics are widely used to control pathogenic microorganisms in both humans and animals. Unfortunately, the widespread use of anti-microbial agents, especially broad spectrum antibiotics, has resulted in a number of serious clinical consequences. For example, the indiscriminate use of these chemicals has resulted in the generation of multiple antibiotic-resistant pathogens. See e.g., Mitchell, P. 1998. *The Lancet* 352: 462–463; Shannon, K., 1998. *The Lancet* 352: 490–491. The initial reports of Meticillin-resistant *Staphylococcus aurous* (MRSA) infections have been overshadowed by the recent outbreaks of Vancomycin-resistant Enterococci (VRE). The development of such resistance has led to numerous reports of systemic infections which remained untreatable with conventional antibiotic therapies. Recently, a Vancomycin- (generally regarded as the antibiotic of last resort) resistant strain of *Staphylococcus aurous* was responsible for over 50 deaths in a single Australian hospital.

Enterococci are currently a major nosocomial pathogen and are likely to remain as such for a long period of time. Enterococci, as well as other microbes, obtain antibiotic resistance genes in several different ways. For example, Enterococci emit pheromones which cause them to become "sticky" and aggregate, thus facilitating the exchange of genetic material, such as plasmids (autonomously replicating, circular DNA which often carry the antibiotic resistance genes). In addition, some Enterococci also possess "conjugative transposons" which are DNA sequences that allow them to directly transfer resistance genes without plasmid intermediary. It is believed that penicillin resistance has been conferred from Enterococci to Streptococci to Staphylococci through this later mechanism.

In addition, antibiotics often kill beneficial, non-pathogenic microorganisms (i.e., flora) within the gastrointestinal tract which contribute to digestive function and health. Accordingly, relapse (the return of infections and their associated symptoms) and secondary opportunistic infections often result from the depletion of lactic acid-producing and other beneficial flora within the gastrointestinal tract. Most, if not all, lactic acid-producing or probiotic bacteria are extremely sensitive to common antibiotic compounds. During a normal course of antibiotic therapy, many individuals develop a number of deleterious physiological side-effects including: diarrhea, intestinal cramping, and sometimes constipation. These side-effects are primarily due to the non-selective action of antibiotics, as antibiotics do not possess the ability to discriminate between beneficial, non-pathogenic and pathogenic bacteria, both bacterial types are killed by these agents. Thus, individuals taking antibiotics offer suffer from gastrointestinal problems as a result of the beneficial microorganisms (i.e., intestinal flora), which normally colonize the gastrointestinal tract, being killed or severely attenuated. The resulting change in the composition of the intestinal flora can result in vitamin deficiencies when the vitamin-producing intestinal bacteria are killed, diarrhea and dehydration and, more seriously, illness should a pathogenic organism overgrow and replace the remaining beneficial gastrointestinal bacteria.

In addition to the gastrointestinal microflora, beneficial and/or pathological microorganisms can also inhabit the oral cavity, the genital area and the vagina (see e.g., Thomason, et al, 1991. *Am. J. Obstet Gynecol.* 165: 1210–1217; Marsh, 1993. *Caries Res.* 27: 72–76; Lehner, 1985. *Vaccine* 3: 65–68; Hill & Embil, 1986. *Can. Med. Assoc. J.* 134: 321–331). The use of anti-microbial drugs can similarly cause an imbalance in those microorganisms and the therapeutic use of probiotic bacteria, especially the Lactobacillus strains, which colonize those areas has been disclosed (see e.g., Winberg, et al., 1993. *Pediatr. Nephrol.* 7: 509–514; Malm, et al., 1996. *Ann. Mar. Metab.* 40: 137–145, U.S. Pat. No. 5,176,911). Increasing numbers of pathogenic microorganisms have developed antibiotic resistance, requiring the development and use of second and third generation antibiotics. Microorganisms that are resistant to multiple drugs have also developed, often with multiple drug resistance spreading between species, leading to serious infections that cannot be controlled by use of antibiotics.

In addition, opportunistic microbial infections often occur in immunodeficient individuals. Immunodeficient individuals have impaired natural immunity allowing pathogenic microorganisms to survive and grow, either internally or externally, due to the individual's diminished immune response to the pathogen. Immunodeficiency can result from genetic conditions, diseases such as AIDS, or therapeutic treatments such as cancer therapy (chemotherapy or radiation treatment) and drug-mediated immunosuppression following organ transplant. Inhibition of pathogenic microorganisms by probiotics is useful for preventing or treating opportunistic infections, particularly in immunodeficient individuals.

Accordingly, there is a need for preventive and therapeutic agents that can control the growth of pathogenic microorganisms without the use of antibiotic chemicals to which the microorganisms already are, or may subsequently become resistant. Probiotics can be applied either internally or externally to restore the balance of beneficial microorganisms to pathogens, without concomitantly contributing to the evolution of drug-resistant pathogens. Lactic acid-producing bacteria (e.g., Bacillus, Lactobacillus and Streptococcus species) have been used as food additives, and there have been som claims that they provide nutritional and therapeutic value (see e.g., Gorbach, 1990. *Ann. Med.* 22: 27–41; Reid, et al., 1990. *Clin. Microbiol. Rev.* 3: 335–344).

In addition, some lactic acid-producing bacteria (e.g., those used to make yogurt) have been suggested to have anti-mutagenic and anti-carcinogenic properties useful in the prevention of human tumors (see e.g., Pool-Zobel, et al., 1993. *Nutr. Cancer* 20: 261–270; U.S. Pat. No. 4,347,240). Some lactic acid-producing bacteria have also been demonstrated to produce bacteriocins, which are inhibitory metabolites responsible for the bacteria's anti-microbial effects (Klaenhammer, 1993. *FEMS Microbiol. Rev.* 12: 39–85; Barefoot & Nettles, 1993. *J. Dairy Sci.* 76: 2366–2379). Selected Lactobacillus strains that produce antibiotics have been disclosed as effective for treatment of infections, sinusitis, hemorrhoids, dental inflammations, and other inflammatory conditions (see U.S. Pat. No. 4,314,995).

Similarly, *Lactobacillus reuteri* has been shown to produce antibiotics with activity against Gram negative and Gram positive bacteria, yeast and a protozoan (see U.S. Pat. No. 5,413,960 and U.S. Pat. No. 5,439,678). *Lactobacillus casei* asp. rhamnosus strain LC-705, DSM 7061, alone or in combination with a Propionibacterium species, in a fermentation broth, has been shown to inhibit yeast and molds in food and silage (U.S. Pat. No. 5,378,458). Furthermore, anti-fungal Serratia species have been added to animal forage and/or silage to preserve the animal feed, particularly *Serratia rubidaea* FB299, alone or combined with an anti-fungal *Bacillus subtilis* (strain P3260). See U.S. Pat. No. 5,371,011), whose disclosure is incorporated herein by reference, in its entirety.

4. Bacillus coagulans

Bacillus coagulansis a non-pathogenic gram positive spore-forming bacteria that produces L(+) lactic acid (dextrorotatory) in homofermentation. This microorganism has been isolated from natural sources, such as heat-treated soil samples inoculated into nutrient medium (see e.g., *Bergey's Manual of Systemic Bacteriology, Vol.* 2, Sneath, P. H. A., et al., eds., (Williams & Wilkins, Baltimore, Md., 1986)). Purified *Bacillus coagulans* strains have served as a source of various enzymes including, but not limited to: restriction endonucleases (see U.S. Pat. No. 5,200,336); amylase (see U.S. Pat. No. 4,980,180); lactase (see U.S. Pat. No. 4,323,651); and cyclo-malto-dextrin glucano-transferase (see U.S. Pat. No. 5,102,800). *Bacillus coagulans* has been used to produce lactic acid (see U.S. Pat. No. 5,079,164). In addition, a strain of *Bacillus coagulans* (designated *Lactobacillus sporogenes*, Sakaguti & Nakayama (ATCC 31284)) has been combined with other lactic acid-producing bacteria and *Bacillus natto* to produce a fermented food product from steamed soybeans (see U.S. Pat. No. 4,110,477). *Bacillus coagulans* strains have also been used as animal feed additives for poultry and livestock to reduce disease and improve feed utilization and to, therefore, increase growth rate in the animals (see International Patent Application Nos. WO 9314187 and WO 9411492).

Accordingly, there remains a need for a highly efficacious biorational therapy which functions to mitigate digestive pathogens, in both humans and animals, by the colonization (or re-colonization) of the gastrointestinal tract with probiotic microorganisms, following the administration of antibiotics, anti-fungal, anti-viral, and similar agents.

5. Dermal Infections

Dermal infections, especially those caused by mycotic pathogens, make-up a considerable percentage of the sale of prescription and over-the-counter medications that are sold annually worldwide. According to the Center for Disease Control and Prevention (CDCP), there is currently a dramatic rise in the number of reported mycotic and bacterial skin infections. Annual sales of dermal and cuticular anti-fungal agents is currently exceeding two billion U.S. dollars each year. Moreover, dermal mycotic illness was recently shown to be increasing at a rate of approximately 9% to 15% per annum, depending upon the specific pathogen and disease. One of the primary factors responsible for the growth of these markets is the fact that more fungal pathogens are becoming resistant to the commonly-utilized anti-fungal agents each year. Examples of anti-fungal agents which are commonly-utilized, include, but are not limited to: Fluconazole (Diflucan®; Pfizer Pharmaceutical), Intraconazole (Sporonox®; Janssen Pharmaceutical), Miconazole Nitrate, Ketoconazole, Tolnaftate, Lamasil, Griseofulvin, Amphotercin B, and other compounds and the formulations thereof.

New generations of anti-fungal and anti-bacterial drugs and preparations are being developed every year to replace those medication in which pathogens have become resistant. As the search for more effective anti-microbial agents continues, so does the search for "carrying agents" which are utilized to disperse and facilitate penetration of these medications through the various dermal and cuticular membranes and tissues. However, to date there has been little success in finding an agent that is able to penetrate dense cuticular material such as finger/toenails and animal hooves.

Diseases that are most common to human dermal and cuticular membranes include: (i) Candidaiasis (e.g., caused by *Candida albicans, Candida tropicalis, Candida golbratta, Candida parapsilosis*); (ii) Tineal diseases, also known as Athletes Foot (Tinea Pedis), Jock Itch (Tinea Cruis), Scalp Infection (Tinea Capitis), Ring Worm, and Beard infections (Tinea Barbae), are all caused by the Trichophylon species, including, but not limited to: *Trichophyton mentagrophytes*; (iii) diseases which are caused by bacterial pathogens, including, but not limited to: *Pseudomonas aeruginosa, Staphylococcus aerues, Staphylococcus epidermidus*, and *Propionibacterium acnes*; and (iv) diseases which are caused by viral pathogens, including, but not limited to: Herpes simplex I & II, and Herpes zoster. Perhaps one of the most difficult-to-treat diseases of fungal etiology are fungal infections of the toenail or fingernail (i.e., Onychomycosis) due to the inability of the currently-available therapeutic compositions to penetrate the dermis or cuticle. The pathogen most commonly associated with this very difficult to treat disease is *Trichophyton rubrum*.

In animals, the most common dermal fungal disease is Ring Worm. In animal hooves, especially athletic equine, there are several diseases of the hoof that are potentially quite serious and difficult to treat, including: White Line Disease (also known as "Seedy Toe"), Hoof Thrush (another yeast- or Candida-related malady), and Drop Sole. In addition, Clubbed Foot is another dermal fungal disease that is of significant concern to the equine industry.

SUMMARY OF THE INVENTION

The present invention discloses the finding that Bacillus species possess the ability to exhibit probiotic activity in aerobic conditions such as on skin or mucous membrane tissues and thereby treat, control and/or inhibit numerous conditions caused by bacterial, fungal, yeast, and viral infections, or combinations thereof. The present invention discloses therapeutic compositions, articles of manufacture and methods of use for inhibiting various microbial infections caused by bacteria, yeast, fungus or virus, which utilize isolated Bacillus species or *Pseudomonas lindbergii* strain.

There are several Bacillus species useful in the practice of the present invention, including: *Bacillus coagulans, Bacillus subtilis, Bacillus laterosporus* and *Bacillus laevolacticus*. Although exemplary of the present invention, *Bacillus coagulans* is only a model for the other Bacillus species, and therefore the use of this species in the majority of the specific examples provided herein are not to be considered as limiting.

The present invention discloses a composition comprising an isolated Bacillus species or *Pseudomonas lindbergii* strain in a pharmaceutically-acceptable carrier suitable for topical application to skin or mucous membranes of a mammal. In one embodiment of the composition, the Bacillus species is included in the composition in the form of spores. In another embodiment, the Bacillus species is included in the composition in the form of a dried cell mass. In these aforementioned compositions, the carrier may be an emulsion, cream, lotion, paste, gel, oil, ointment, suspension, aerosol spray, powder, aerosol powder or semi-solid formulation. In a preferred embodiment of the present invention, a therapeutic composition comprising an extracellular product of a *Bacillus coagulans* species in a pharmaceutically-acceptable carrier suitable for topical application to skin or a mucosal membrane of a mammal is disclosed. In this preferred embodiment, the extracellular product comprises the supernatant or filtrate of a culture of an isolated *Bacillus coagulans* species. The carrier may be an emulsion, paste, cream, lotion, gel, oil, ointment, suspension, aerosol spray, powder, aerosol powder, or semi-solid formulation.

In another preferred embodiment of the present invention, an extracellular product of *Pseudomonas lindbergii* strain comprising a supernatant or filtrate of a culture of said *Pseudomonas lindbergii* strain is utilized as a therapeutic composition for the prevention and/or control of infections caused by bacterium, fungi, yeast, and virus, and combinations thereof. The therapeutic composition is comprised of the extracellular product of the *Pseudomonas lindbergii* strain in a pharmaceutically-acceptable carrier suitable for topical application to skin or a mucosal membrane of a mammal is disclosed. The carrier may be an emulsion, cream, lotion, gel, oil, ointment, suspension, aerosol spray, powder, aerosol powder, or semi-solid formulation.

According to another aspect of the invention, there is provided a method of preventing bacterial, yeast, fungal or viral infection, including the steps of applying topically to skin or a mucous membrane of a mammal a probiotic composition comprising an isolated Bacillus species; and allowing the probiotic bacteria Bacillus species to grow topically for sufficient time to inhibit growth of bacteria, yeast, fungus or virus. An additional embodiment further includes the steps of providing spores of the Bacillus species in the probiotic composition, and allowing the spores to germinate after the applying step. In yet another embodiment, the step of allowing the Bacillus species to grow inhibits growth of one or more microbe species selected from the group consisting of Staphylococcus species, Streptococcus species, Pseudomonas species, *Escherichia coli, Gardnerella vaginalis, Propionibacterium acnes*, Blastomyces species, *Pneumocystis carinii, Aeromonas hydrophilia*, Trichosporon species, Aspergillus species, Proteus species, Acremonium species, Cryptococcus neoformans, Microsporum species, Aerobacter species, Clostridium species, Klebsiella species, Candida species and Trichophyton species. Also inhibited are certain virus species (e.g., Herpes simplex I and II, and Herpes zoster). In still another embodiment, the applying step is applying a probiotic composition in the form of a cream, lotion, gel, oil, ointment, suspension, aerosol spray, powder, aerosol powder or semi-solid formulation.

In further embodiments of the present invention, methods for inhibiting growth of bacteria, yeast, fungus, virus or a combination thereof, are provided, and include the steps of applying topically to skin or a mucous membrane a composition comprising an extracellular product of an isolated *Bacillus coagulans* or *Pseudomonas lindbergii* strain, and allowing the composition to be present for sufficient time to inhibit growth of bacteria, yeast, fungus, virus or any combination thereof. In one embodiment, the applying step includes applying the composition in the form of a cream, lotion, gel, oil, ointment, suspension, aerosol spray, powder, aerosol powder or semi-solid formulation.

According to yet another aspect of the invention, there is provided a composition comprising an isolated Bacillus species is applied to a flexible article that is intended to be worn by or attached to skin or a mucous membrane of a mammal to allow probiotic activity of the bacteria to occur adjacent to or on the skin or mucous membrane.

In another embodiment of the invention, there is provided a method of inhibiting growth of bacteria, yeast, fungus, virus or any combination thereof, including the steps of applying a composition comprising an isolated Bacillus species to a solid surface, contacting the solid surface with the applied Bacillus species thereon to skin or a mucous membrane of a mammal, and allowing the solid surface to contact the skin or mucous membrane for sufficient time to allow initiation of probiotic activity of the isolated bacteria to inhibit growth of bacteria, yeast, fungus, virus or a combination thereof adjacent to or on the skin or mucous membrane. In one embodiment, the applying step includes applying the composition to a diaper, pliable material for wiping skin or a mucous membrane, dermal patch, adhesive tape, absorbent pad, tampon or article of clothing. In another embodiment, the applying step includes impregnating the composition into a fibrous or non-fibrous solid matrix.

The present invention also discloses a therapeutic system for treating, reducing or controlling microbial infections comprising a container comprising a label and a therapeutic composition as described herein, wherein said label comprises instructions for use of the composition for treating infection.

The present invention provides several advantages. In particular, insofar as there is a detrimental effect to the use of antibiotics because of the potential to produce antibiotic-resistant microbial species, it is desirable to have an anti-microbial therapy which does not utilize conventional anti-microbial reagents. The present invention does not contribute to the production of future generation of antibiotic resistant pathogens.

It should be understood that both the foregoing general description and the following detailed description are exemplary and explanatory only and are not restrictive of the invention as claimed.

DESCRIPTION OF THE FIGURES

FIG. 1: illustrates various metabolic activities and the associated, characteristic physiological or biochemical response in *Bacillus coagulans*.

FIG. 2: illustrates the various pathogens, which may be treated by use of the therapeutic compositions of the present invention, and their associated disorders.

FIG. 3: enumerates the tested fungal strains of Trichophyton species (available from the American Type Culture Collection (ATCC; Manassas, Va.)), their respective ATCC accession numbers, and the results of in vitro inhibition by *Bacillus coagulans*.

FIG. 4: enumerates the tested yeast strains of ability of Candida species (available from the American Type Culture Collection (ATCC; Manassas, Va.)), their respective ATCC accession numbers, and the results of in vitro inhibition by *Bacillus coagulans*.

FIG. 11: illustrates, in tabular form, a comparison of the anti-mycotic, Fluconazole with *Bacillus coagulans* and *Pseudomonas lindbergii* supernatants (generically designated Ganeden Supernatant) in the inhibition of various bacterial, fungal, and yeast species.

DETAILED DESCRIPTION OF THE INVENTION

Figure 5A:
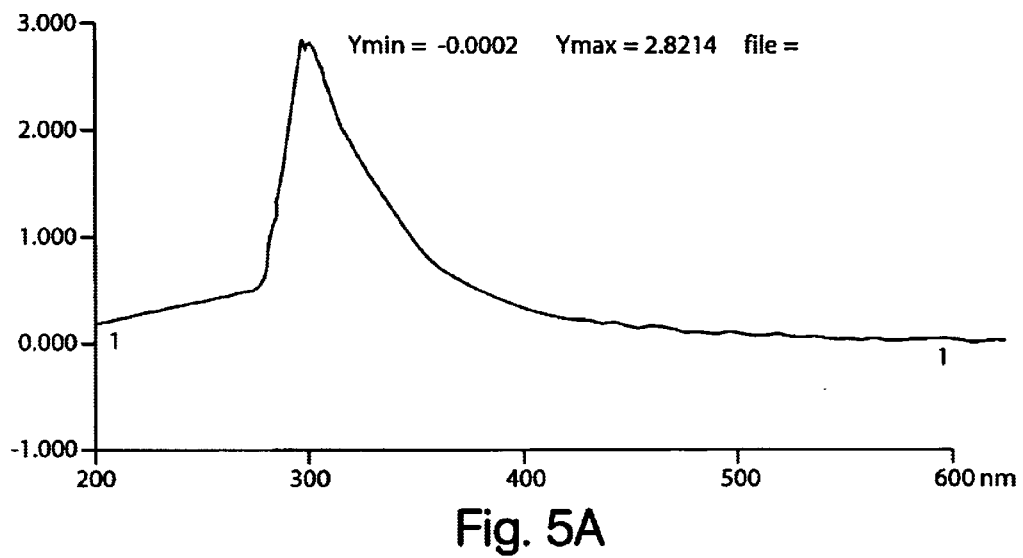
FIG. 5: illustrates a wavelength scan of *Bacillus coagulans* (Panel A) and *Pseudomonas lindbergii* (Panel B) supernatants with a water blank.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated by reference.

As utilized herein, the term "probiotic" refers to microorganisms (e.g., bacteria, yeast, viruses, and/or fungi) which form, at a minimum, a part of the transient or endogenous flora and, thus, possess a beneficial prophylactic and/or therapeutic effect upon the host organism. Probiotics are generally known to be clinically-safe (i.e., non-pathogenic) by those skilled within the art. Although not wishing to be bound by any particular mechanism, the probiotic activity of Bacillus species is thought to result from competitive inhibition of growth of pathogens due to superior colonization, parasitism of undesirable microorganisms, lactic acid production and/or other extracellular products having anti-microbial activity, or combinations thereof.

As utilized herein, the term "microbial" refers to bacteria, yeast, fungi, and/or virus.

The present invention discloses the ability to utilize Bacillus species in therapeutic compositions as a probiotic, for the prevention and/or control infections caused by pathogens including, but not limited to, microbial, yeast, fungal, or viral infections. As will be discussed infra, these compositions can be formulated in a variety of configurations, due to the fact that the bacterium is presented as a viable organism, either as a vegetative cell or as a spore, and colonizes the tissue of interest. Specifically, the cells/spores may be presented in therapeutic compositions suited for topical application to a tissue, or in suspensions such as a bath, or on flexible materials such as diapers, bandaids, tampons, and like personal articles, all directed to the objective of introducing the bacteria topically to skin or a mucous membrane tissue.

1. Probiotic, Lactic Acid-Producing Bacillus Strains

By way of example, and not of limitation to any particular mechanism, the prophylactic and/or therapeutic effect of a lactic acid-producing bacteria of the present invention results, in part, from a competitive inhibition of the growth of pathogens due to: (i) their superior colonization abilities; (ii) parasitism of undesirable microorganisms; (iii) the production of lactic acid and/or other extracellular products possessing anti-microbial activity; or (iv) various combinations thereof. It should be noted that the aforementioned products and activities of the lactic acid-producing Bacillus of the present invention act synergistically to produce the beneficial probiotic effect disclosed herein.

A probiotic bacteria which is suitable for use in the methods and compositions of the present invention: (i) possesses the ability to produce lactic acid; (ii) demonstrates beneficial function; and (iii) is non-pathogenic. By way of example and not of limitation, many suitable bacteria have been identified and are described herein, although it should be noted that the present invention is not to be limited to currently-classified bacterial species insofar as the purposes and objectives as disclosed. The physiochemical results from the in vivo production of lactic acid is key to the effectiveness of the probiotic lactic acid-producing bacteria of the present invention. Lactic acid production markedly decreases the pH (i.e., increases acidity) within the local micro-floral environment and does not contribute to the growth of many undesirable, physiologically-deleterious bacteria, fungi, and viruses. Thus, by the mechanism of lactic acid production, the probiotic inhibits growth of competing pathogenic bacteria.

Typical lactic acid-producing bacteria useful as a probiotic of this invention are efficient lactic acid producers which include non-pathogenic members of the Bacillus genus which produce bacteriocins or other compounds which inhibit the growth of pathogenic organisms. Exemplary lactic acid-producing, non-pathogenic Bacillus species include, but are not limited to: *Bacillus coagulans; Bacillus coagulans* Hammer; and *Bacillus brevis* subspecies *coagulans*.

Several Bacillus species which are preferred in the practice of the present invention, include, but are not limited to the lactic acid-producing *Bacillus coagulans* and *Bacillus laevolacticus*. Various other non-lactic acid-producing Bacillus species may be utilized in the present invention so long as they produce compounds which possess the ability to inhibit pathogenic bacterial or mycotic growth. Examples of such suitable non-lactic acid-producing Bacillus include, but are not limited to: *Bacillus subtilis, Bacillus uniflagellatus, Bacillus lateropsorus, Bacillus laterosporus* BOD, *Bacillus megaterium, Bacillus polymyxa, Bacillus licheniformis, Bacillus pumilus, Bacillus mycoides,* and *Bacillus sterothermophilus*.

The Bacillus species, particularly those species having the ability to form spores (e.g., *Bacillus coagulans*), are a preferred embodiment of the present invention. The Bacillus species utilized in the practice of the present invention may selected from the group comprising: *Bacillus coagulans, Bacillus subtilis, Bacillus laterosporus* and *Bacillus laevolacticus*, all of which have the ability to form spores, and can colonize tissue aerobically. There are a variety of different Bacillus species, including, but not limited to many different strains available through commercial and public sources, such as the American Tissue Culture Collection (ATCC). For example, *Bacillus coagulans* strains are available as ATCC Accession Numbers 15949, 8038, 35670, 11369, 23498, 51232, 11014, 31284, 12245, 10545 and 7050. *Bacillus subtilis* strains are available as ATCC Accession Numbers 10783, 15818, 15819, 27505, 13542, 15575, 33234, 9943, 6051a, 25369, 11838, 15811, 27370, 7003, 15563, 4944, 27689, 43223, 55033, 49822, 15561, 15562, 49760, 13933, 29056, 6537, 21359, 21360, 7067, 21394, 15244, 7060, 14593, 9799, 31002, 31003, 31004, 7480, 9858, 13407, 21554, 21555, 27328 and 31524. *Bacillus laterosporus* strains are available as ATCC Accession Numbers 6456, 6457, 30 29653, 9141, 533694, 31932 and 64, including *Bacillus laterosporus* BOD. *Bacillus laevolacticus* strains are available as ATCC Accession Numbers 23495, 23493, 23494, 23549 and 23492. It should be noted, however, that although many of the examples herein refer to the *Bacillus coagulans* species in particular, it is intended that any of the Bacillus species can be used in the compositions, articles of manufacture, systems and method of the present invention.

A Bacillus species is particularly suited for the present invention due to the properties in common between species of the Bacillus genus, including, but not limited to, the ability to form spores which are relatively resistant to heat and other conditions, making them ideal for storage (shelf-life) in product formulations, and ideal for survival and colonization of tissues under conditions of pH, salinity, and the like on tissues subjected to microbial infection. For example, probiotic *Bacillus coagulans* is non-pathogenic and is generally regarded as safe (i.e., GRAS classification) by the U.S. Federal Drug Administration (FDA) and the U.S. Department of Agriculture (USDA), and by those individuals skilled within the art. Additional useful characteristics of the Bacillus species include, but are not limited to: non-pathogenicity, being aerobic, facultative and heterotrophic, thus rendering these species safe, and able to colonize skin, mucous membrane tissues, and various other tissues of interest.

Because Bacillus species possesses the ability to produce heat-resistant spores, it is particularly useful for making pharmaceutical compositions which require heat and pressure in their manufacture. Accordingly, formulations that include the utilization viable Bacillus spores in a pharmaceutically-acceptable carrier are particularly preferred for making and using compositions disclosed in the present invention. The growth of these various Bacillus species to form cell cultures, cell pastes, and spore preparations is generally well-known within the art. It should also be noted that the exemplary culture and preparative methods which are described herein for *Bacillus coagulans* may be readily utilized and/or modified for growth and preparation of the other Bacillus strains, as well as the lactic acid-producing bacteria disclosed in the present invention. In addition, the exemplary methods and compositions which are described herein using *Bacillus coagulans* as a probiotic for controlling, treating, or reducing microbial infections, may also be readily utilized with other Bacillus species.

2. *Bacillus coagulans* Compositions

Although, as disclosed herein, any of the aforementioned Bacillus strains may be utilized in the practice of the present invention, purified *Bacillus coagulans* is exemplary and preferred as a probiotic for biological control of various microbial pathogens. Because *Bacillus coagulans* forms heat-resistant spores, it is particularly useful for making pharmaceutical compositions for treating microbial infections. Topical formulations which include viable *Bacillus coagulans* spores in a pharmaceutically-acceptable carrier, are particularly preferred for making and using preventive and therapeutic compositions of the present invention. The term "topical" is broadly utilized herein to include both epidermal and/or skin surfaces, as well as mucosal surfaces of the body.

2.1 Characteristics and Sources of *Bacillus coagulans*

The Gram positive rods of *Bacillus coagulans* have a cell diameter of greater than 1.0 μm with variable swelling of the sporangium, without parasporal crystal production. *Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., *Bergey's Manual of Systemic Bacteriology*, Vol. 2, Sneath, P. H. A. et al., eds., Williams & Wilkins, Baltimore, Md., 1986). Purified *Bacillus coagulans* strains have served as a source of enzymes including endonucleases (e.g., U.S. Pat. No. 5,200,336); amylase (U.S. Pat. No. 4,980,180); lactase (U.S. Pat. No. 4,323,651) and cyclo-malto-dextrin glucano-transferase (U.S. Pat. No. 5,102,800). *Bacillus coagulans* has also been utilized to produce lactic acid (U.S. Pat. No. 5,079,164). A strain of *Bacillus coagulans* (also referred to as *Lactobacillus sporogenes*; Sakaguti & Nakayama, ATCC No. 31284) has been combined with other lactic acid producing bacteria and Bacillus natto to produce a fermented food product from steamed soybeans (U.S. Pat. No. 4,110,477). *Bacillus coagulans* strains have also been used as animal feeds additives for poultry and livestock to reduce. disease and improve feed utilization and, therefore, to increase growth rate in the animals (International PCT Patent Applications No. WO 9314187 and No. WO 9411492). In particular, *Bacillus coagulans* strains have been used as general nutritional supplements and agents to control constipation and diarrhea in humans and animals.

Purified *Bacillus coagulans* bacteria utilized in the present invention are available from the American Type Culture Collection (ATCC, Manassas, Va.) using the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284); and *Bacillus coagulans* Hammer NCA 4259 (ATCC No. 15949). Purified *Bacillus coagulans* bacteria are also available from the Deutsche Sarumlung von Mikroorganismen und Zelikuturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384, corresponds to ATCC No. 11369); and *Bacillus coagulans* Hammer (DSM No. 2385, corresponds to ATCC No. 15949). *Bacillus coagulans* bacteria can also be obtained from commercial suppliers such as Sabinsa Corporation (Piscataway, N.J.) or K.K. Fermentation (Kyoto, Japan).

*Bacillus coagulans* strains and their growth requirements have been described previously (see e.g., Baker, D. et al, 1960. *Can. J. Microbiol.* 6: 557–563; Nakamura, H. et al, 1988. *Int. J. Syst. Bacteriol.* 38: 63–73. In addition, various strains of *Bacillus coagulans* can also be isolated from natural sources (e.g., heat-treated soil samples) using well-known procedures (see e.g., *Bergey's Manual of Systemic Bacteriology*, Vol. 2, p. 1117, Sneath, P. H. A. et al., eds., Williams & Wilkins, Baltimore, Md., 1986).

It should be noted that *Bacillus coagulans* had previously been mis-characterized as a Lactobacillus in view of the fact that, as originally described, this bacterium was labeled as *Lactobacillus sporogenes* (See Nakamura et al. 1988. *Int. J. Syst. Bacteriol.* 38: 63–73). However, initial classification was incorrect due to the fact that *Bacillus coagulans* produces spores and through metabolism excretes L(+)-lactic acid, both aspects which provide key features to its utility. Instead, these developmental and metabolic aspects required that the bacterium be classified as a lactic acid bacillus, and therefore it was re-designated. In addition, it is not generally appreciated that classic Lactobacillus species are unsuitable for colonization of the gut due to their instability in the harsh (i.e., acidic) pH environment of the bile, particularly human bile. In contrast, *Bacillus coagulans* is able to survive and colonize the gastrointestinal tract in the bile environment and even grown in this low pH range. In particular, the human bile environment is different from the bile environment of animal models, and heretofore there has not been any accurate descriptions of *Bacillus coagulans* growth in human gastrointestinal tract models.

2.2 Growth of *Bacillus coagulans*

Bacillus coagulansis aerobic and facultative, grown typically in nutrient broth, pH 5.7 to 6.8, containing up to 2% (by wt) NaCl, although neither NaCl nor KCl are an absolute requirement for growth. A pH value ranging from approximately pH 4 to pH 6 is optimum for initiation of sporulation. It is optimally grown at about 30° C. to about 55° C., and the spores can withstand pasteurization. It exhibits facultative and heterotrophic growth by utilizing a nitrate or sulfate source. Additional metabolic characteristics of *Bacillus coagulans* are summarized in FIG. 1.

*Bacillus coagulans* can be grown in a variety of media, although it has been found that certain growth conditions produce a culture which yields a high level of sporulation. For example, sporulation is enhanced if the culture medium includes 10 mg/liter of manganese sulfate, yielding a ratio of spores to vegetative cells of about 80:20. In addition, certain growth conditions produce a bacterial spore which contains a spectrum of metabolic enzymes particularly suited for the present invention (i.e., the control of microbial infections). Although spores produced by these particular growth conditions are preferred, spores produced by any compatible growth conditions are suitable for producing a *Bacillus coagulans* useful in the present invention. It should also be noted that the most preferred embodiment of the present invention utilizes *Bacillus coagulans* in spore, rather than vegetative bacterial form.

The preparation of a *Bacillus coagulans* vegetative bacteria and spores will be more fully described in the Specific Examples section, infra.

3. Extracellular Products Possessing Anti-Microbial Activity

*Bacillus coagulans* cultures contain secreted products which possess anti-microbial activity. These secreted products are useful in therapeutic compositions according to the present invention. Cell cultures are harvested as described above, and the culture supernatants are collected, by filtration or centrifugation, or both, and the resulting supernatant contains anti-microbial activity useful in the therapeutic compositions of the present invention.

The preparation of a *Bacillus coagulans* extracellular products will be more fully described in the Specific Examples section, infra.

4. Probiotic Activity of *Bacillus coagulans*

It is well-documented clinically that many species of bacterial, mycotic and yeast pathogens possess the ability to cause a variety of disorders. Therefore, the utilization of the probiotic microorganism-containing compositions of the present invention inhibits these pathogens are useful in the prophylactic or therapeutic treatment of conditions associated with infection by these aforementioned pathogens.

Pathogenic bacteria inhibited by *Bacillus coagulans* activity include, for example, *Staphylococcus aureus, Staphylococcus epidermidis, Streptococcus pyogenes, Pseudomonas aeruginosa, Escherichia coli*(i.e., enterohemorragic species), numerous Clostridium species (e.g., *Clostridium perfingens, Clostridium botulinum, Clostridium tributrycum, Clostridium sporogenes*, and the like); *Gardnereia vaginails; Proponbacterium acnes; Aeromonas hydrophia*; Aspergillus species; Proteus species; and Klebsiella species.

Pathogenic yeast and other fungi inhibited by *Bacillus coagulans* activity include *Candida albicans, Candida tropicalis* and *Trichophyton mentagrophytes, Trichophyton interdigitale, Trichophyton rubrum*, and *Trichophyton yaoundei*.

*Bacillus coagulans* has also been demonstrated to inhibit Herpes simplex viruses I (HSV-I; oral "cold sores" and Herpetic Whitlow) and Herpes simplex II (HSV-II; genital herpes) and Herpes zoster (shingles) infections.

These aforementioned pathogens have been associated with a variety of disorders including, but not limited to: diaper rash; oral, genital, cervical and vaginal yeast infections; toxic shock syndrome; chronic mucocutaneous candidaiasis; dermatophytosis; bacterial vaginosis; tineal fungal infections (e.g., ringworm, athlete's foot, and jock itch); scalp and nail fungal infections; superficial skin disorders (e.g., erysipelas, open-wound infections, acne, abscess, boil, eczema, dermatitis, contact dermatitis, hypersensitinitis, contact lesions, bed sores, and diabetic lesions); miscellaneous opportunistic infections; oral and genital viral lesions, and the like conditions as are well known in the art. Therefore, topical use of compositions containing the *Bacillus coagulans* active agents that inhibit these pathogens are useful in preventing or treating these conditions.

The various pathogens, which may be treated by use of the therapeutic compositions of the present invention, and their associated disorders are illustrated in FIG. 2. It should be noted, however, that the pathogens listed in FIG. 2 are set forth as examples only, and are not meant to be limiting to the types of organisms which can be treated by use of the methodologies or compositions of the present invention. Accordingly, various other skin- and mucous membrane-infecting microbes and dermatophytes can also be treated by use of the present compositions and methods disclosed herein.

The aforementioned anti-microbial activity of a therapeutic composition of the present invention will be more fully-described in the Specific Examples section, infra.

5. Bifidogenic Oligosaccharides

Bifidogenic oligosaccharides, as designated herein, are a class of carbohydrates particularly useful for preferentially promoting the growth of a lactic acid-producing bacteria of the present invention. These oligosaccharides include, but are not limited to: fructo-oligosaccharides (FOS); glucooligosaccharides (GOS); other long-chain oligosaccharide polymers of fructose and/or glucose; and the trisaccharide—raffinose. All of these aforementioned carbohydrates are not readily digested by pathogenic bacteria. Thus, the preferential growth of lactic acid-producing bacteria is promoted by the utilization of these bifidogenic oligosaccharides due to the nutrient requirements of this class of bacterium, as compared to pathogenic bacteria.

Bifidogenic oligosaccharides are long chain polymers that are utilized almost exclusively by the indigenous Bifidobacteria and Lactobacillus in the intestinal tract and can be similarly utilized by Bacillus. In contrast, physiologically deleterious bacteria such as Clostridium, Staphylococcus, Salmonella and *Escherichia coli*cannot metabolize FOS, or other bifidogenic oligosaccharides, and therefor use of these bifidogenic oligosaccharides in combination with a lactic acid-producing bacteria of the present, preferably *Bacillus coagulans*, allows these beneficial, probiotic bacteria to grow and effectively compete with, and eventually replace any undesirable, pathogenic microorganisms within the gastrointestinal tract.

The use of bifidogenic oligosaccharides in the compositions of the present invention provides a synergistic effect thereby increasing the effectiveness of the probiotic-containing compositions disclosed herein. This synergy is manifested by selectively increasing the ability of the probiotic bacterium to grow by, for example, increasing the level of nutrient supplementation which preferentially selects for growth of the probiotic bacteria over many other bacterial species within the infected tissue.

In addition, it is readily understood that Bifidobacteria and Lactobacillus are also producers of lactic acid. Bifidogenic oligosaccharides enable these aforementioned probiotic organisms to proliferate preferentially over the undesirable bacteria within the gastrointestinal tract, thereby augmenting the probiotic state of the body by further enhancing the solubility of these nutrients (whether of food origin or as a result of nutritional supplement augmentation). Thus, the presence of the bifidogenic oligosaccharides in the compositions of the present invention allows for more effective microbial inhibition by increasing the ability of all varieties of probiotic bacteria to grow, and therefore provide said benefit.

The bifidogenic oligosaccharide of the present invention may be used either alone, or in combination with a lactic acid-producing microorganisms in a therapeutic composition. More specifically, due to the growth promoting activity of bifidogenic oligosaccharides, the present invention contemplates a composition comprising a bifidogenic oligosaccharide present in a concentration sufficient to promote the growth of lactic acid-producing microorganisms. As shown herein, these concentrations amounts can vary widely, as the probiotic microorganisms will respond to any metabolic amount of nutrient oligosaccharide, and therefore the present invention need not be so limited.

A preferred and exemplary bifidogenic oligosaccharide is fructo-oligosaccharide (FOS), although other carbohydrates may also be utilized, either alone or in combination. FOS can be obtained from a variety of natural sources, including commercial suppliers. As a product isolated from natural sources, the components can vary widely and still provide the beneficial agent, namely FOS. FOS typically has a polymer chain length of from about 4 to 200 sugar units, with the longer lengths being preferred. For example, the degree of purity can vary widely so long as biologically-functional FOS is present in the final formulation. Preferred FOS formulations contain at least 50% by weight of fructo-oligosaccharides compared to simple(mono or disaccharide) sugars such as glucose, fructose or sucrose, preferably at least 80% fructo-oligosaccharides (FOS), more preferably at least 90% and most preferably at least 95% FOS. Sugar content and composition can be determined by any of a variety of complex carbohydrate analytical detection methods as is well known. Preferred sources of FOS include, but are not limited to: inulin; Frutafit IQ™ (Imperial Suiker Unie; Sugar Land, Tex.); NutraFlora™ (Americal Ingredients, Inc.; Anaheim, Calif.); and Fruittrimfat Replacers and Sweeteners (Emeryville, Calif.). Bifidogenic oligosaccharides such as GOS, and other long chain oligosaccharides are also available from commercial vendors.

6. Therapeutic Compositions

Compositions of the present invention which are suitable for use in preventing, treating, and/or controlling microbial infections comprise an active ingredient, specifically: (i) a Bacillus species bacterium (e.g., vegetative cell) or spore; (ii) vegetative cells or spores of *Bacillus coagulans*; (iii) extracellular anti-microbial or antibiotic metabolites of *Bacillus coagulans*; or (iv) combinations thereof in various formulations.

The active Bacillus ingredients comprise about 0.1% to about 50% by weight of the final composition, preferably 1% to 10% by weight, in a formulation suitable for topical administration.

The formulation for a therapeutic composition of this invention may include other probiotic agents or nutrients for promoting spore germination and/or Bacillus growth. The compositions may also include known anti-microbial, antiviral, anti-fungal, or anti-yeast agents, all of which must be compatible with maintaining viability of the specific Bacillus active agent, when Bacillus organisms or spores are utilized as the active agent. The various other agents within the therapeutic compositions of the present invention may either be synergists or active agents. In a preferred embodiment, the known anti-microbial, anti-viral, antiyeast, and/or anti-fungal agents are probiotic agents compatible with Bacillus. The therapeutic compositions may also include, but are not limited to the inclusion of: known antioxidants (e.g., vitamin E); buffering agents; lubricants (e.g., synthetic or natural beeswax); sunscreens (e.g., paraaminobenzoic acid); and other cosmetic agents (e.g., coloring agents, fragrances, oils, essential oils, moisturizers or drying agents). Thickening agents (e.g., polyvinylpyrrolidone, polyethylene glycol or carboxymethyicellulose) may also be added to the compositions.

Fragrances and essential oils are particularly suited for the compositions used in personal hygiene products and methods, and can include sea salts, herbs or herb extracts, fragrance oils from a large variety of plants or animals, and fragrances from a large variety of plants or animals, as are all well known. Preferred fragrances useful in a composition of this invention include African violet, frankincense & myrrh, lavender, vanilla, gardenia, honeysuckle, sandalwood, musk, jasmine, lotus, orange blossom, patchouli, heather, magnolia, amber, rose, and the like fragrances. Preferred oils, including essential or fragrant oils, include almond, aloe, amber, apple, apricot, bayberry, benzion, cactus blossom, carnation, carrageenan, cedarwood, cinnamon, cloves, coconut, cedar, copal, Emu, eucalyptus, franfipani, frankincense and myrrh, gardenia, grapefruit, heather, herbs, honeysuckle, jasmine, jojoba, kelp, lavender, lemon, lilac, lotus, magnolia, mulberry, musk, myrrh, narcissus, orange blossom, patchoull, peach, pinon pine, plumeria, rose, rosemary, safflower, sage, sandalwood, spirulina, strawberry, vanilla, violet, wisteria, and the like oils. It should be noted that a particularly preferred oil for use in the topically-administered therapeutic compositions of the present invention is Emu oil, which is generally utilized in a concentration of approximately 1% to 75% by weight. The use of Emu oil in the therapeutic compositions of the present invention will be more fully discussed, infra.

In addition, the fragrances and essential oils can be provided in various bath salt and bath soap compositions. Salts and soaps are also well-known within the art and can include sea salts, desert salts, mineral salts, sodium sesquicarbonate, magnesium sulfate, and the like commonly used bath salts.

Fragrances, oils, and salts are well known in the art, can be obtained from a variety of natural and commercial sources, and are not considered to limiting to the present invention. Exemplary commercial sources include: Innovative Body Science (Carlsbad, Calif.); Scents of Paradise - SunBurst Technology, Inc., (Salem, Oreg.); Intercontinental Fragrances, Inc., (Houston, Tex.); Scentastics, Inc., (Ft. Lauderdale, Fla.); and Michael Giordano International, Inc., (North Miami, Fla.).

Chemicals used in the present compositions can be obtained from a variety of commercial sources, including Spectrum Quality Products, Inc (Gardena, Calif.); Seltzer Chemicals, Inc., (Carlsbad, Calif.); and Jarchem Industries, Inc., (Newark, N.J.).

In the therapeutic compositions of the present invention, the active agents are combined with a "carrier" which is physiologically compatible with the skin, membrane, or mucosal tissue of a human or animal to which it is topically administered. Specifically, in the preferred embodiment, the carrier is substantially inactive, with the exception of its intrinsic surfactant properties which are used in the production of a suspension of the active ingredients. The compositions may include other physiologically active constituents that do not interfere with the efficacy of the active agents in the composition.

A typical therapeutic composition of the present invention will contain in a one gram dosage formulation, from approximately $1 \times 10^3$ to $1 \times 10^{12}$, and preferably approximately $2 \times 10^5$ to $1 \times 10^{10}$, colony forming units (CFU) of viable Bacillus bacteria (i.e., vegetative bacteria) or bacterial spores. In one preferred embodiment, the therapeutic composition of the present invention may also include from approximately 10 mg to one gram of a bifidogenic oligosaccharide (e.g., a fructo-oligosaccharide). The formulation may be completed in total weight by use of any of a variety of carriers and/or binders. For example, a preferred carrier is micro-crystalline cellulose (MCC), which is added in a concentration sufficient to complete the typical one gram dosage total weight. Particularly preferred formulations of the therapeutic composition of the present invention will be fully-described in the Specific Examples section, infra.

The carriers utilized in the therapeutic compositions of the present invention may be solid-based, dry materials for use in powdered formulations or, alternately, may be liquid or gel-based materials for use in liquid or gel formulations. The specific formulations depend, in part, upon the routes or modes of administration.

Typical carriers for dry formulations include, but are not limited to, trehalose, malto-dextrin, rice flour, micro-crystalline cellulose (MCC), magnesium sterate, inositol, fructo-oligosaccharides FOS, gluco-oligosaccharides (GOS), dextrose, sucrose, talc, and the like carriers. Where the composition is dry and includes evaporated oils that produce a tendency for the composition to cake (i.e., adherence of the component spores, salts, powders and oils), it is preferable to include dry fillers which both distribute the components and prevent caking. Exemplary anti-caking agents include MCC, talc, diatomaceous earth, amorphous silica and the like, typically added in an concentration of from approximately 1% to 95% by-weight.

Suitable liquid or gel-based carriers are well-known in the art (e.g., water, physiological salt solutions, urea, methanol, ethanol, propanol, butanol, ethylene glycol and propylene glycol, and the like). Preferably, water-based carriers are approximately neutral pH.

Suitable carriers include aqueous and oleaginous carries such as, for example, white petrolatum, isopropyl myristate, lanolin or lanolin alcohols, mineral oil, fragrant or essential oil, nasturtium extract oil, sorbitan mono-oleate, propylene glycol, cetylstearyl alcohol (together or in various combinations), hydroxypropyl cellulose (MW=100,000 to 1,000,000), detergents (e.g., polyoxyl stearate or sodium lauryl sulfate) and mixed with water to form a lotion, gel, cream or semi-solid composition. Other suitable carriers comprise water-in-oil or oil-in-water emulsions and mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. For example, emulsions containing water, glycerol stearate, glycerin, mineral oil, synthetic spermaceti, cetyl alcohol, butylparaben, propylparaben and methylparaben are commercially available. Preservatives may also be included in the carrier including methylparaben, propylparaben, benzyl alcohol and ethylene diamine tetraacetate salts. Well-known flavorings and/or colorants may also be included in the carrier. The composition may also include a plasticizer such as glycerol or polyethylene glycol (MW 400 to 20,000). The composition of the carrier can be varied so long as it does not interfere significantly with the pharmacological activity of the active ingredients or the viability of the Bacillus cells or spores.

A therapeutic composition of the present invention may be formulated to be suitable for application in a variety of manners, for example, in a cream for topical application to the skin (e.g., for ringworm or athlete's foot), in a wash for the mouth (e.g., for oral thrush), in a douche for vaginal application (e.g., for vaginitis), in a powder for chaffing (e.g., for dermatitis), in a liquid for toe nails (e.g., for tinea pedis), in a bath salt or bath powder for treating genital, foot or other tissue infections in a bath, and the like. Other formulations will be readily apparent to one skilled in the art and will be discussed more fully in the Specific Examples section, infra.

6.1 Therapeutic Methods for Treatment of Microbial Infections

The present invention discloses methodologies for treating, reducing, and/or controlling microbial infections in a variety of skin and mucosal membrane tissues using a therapeutic composition or therapeutic article of manufacture of this invention. Optimally the compositions effectively reduce the bacterial, yeast, fungal and/or viral titer in the treated individual, particularly at the site of application of the topical composition. For example, the pathogenic microbial titer in lesions has been demonstrated to be significantly reduced following the topical administration of the therapeutic composition of the present invention to the affected area(s) of the skin or mucous membrane. The disclosed methods of treatment also reduce symptoms of pathogenic microbial infection (e.g., pain associated with infected or microbial-caused lesions) and promote more rapid healing than would be found without Bacillus treatment.

The method of the present invention includes administration of a composition containing the active Bacillus ingredient to a human or animal to treat or prevent microbial (i.e., bacterial, yeast, fungal or viral) infection. Administration is preferably to the skin or a mucous membrane using a cream, lotion, gel, oil, ointment, suspension, aerosol spray, powder, semi-solid formulation (e.g., a suppository), or article of manufacture, all formulated so as to contain a therapeutic composition of the present invention using methods well-known in the art.

Application of the therapeutic composition of the present invention, containing the active Bacillus agent effective in preventing or treating a microbial infection, generally consists of one to ten applications of a 10 mg to 10 g concentration of a composition per application, for a time period of one day up to one month. Applications are generally once every twelve hours and up to once every four hours. Preferably, two to four applications of the therapeutic composition per day, of about 0.1 g to 5 g concentration per application, for one to seven days are sufficient to prevent or treat a microbial infection. For topical applications, the therapeutic compositions are preferably applied to lesions daily as soon as symptomology (e.g., pain, swelling or inflammation) is detected. The specific route, dosage, and timing of the administration will depend, in part, on the particular pathogen and/or condition being treated, as well as the extent of the condition.

A preferred methodology involves the application of from approximately $1 \times 10^3$ to $1 \times 10^2$ viable bacterium or spores per day, preferably from approximately $1 \times 10^5$ to $1 \times 10^{10}$ viable bacterium or spores per day, and more preferably about from approximately $5 \times 10^8$ to $1 \times 10^9$ viable bacterium or spores per day. In addition, a preferred method optionally comprises application of a therapeutic composition that additionally contains from approximately 10 mg to 20 g of fructo-oligosaccharide (FOS) per day, preferably from approximately 50 mg to 10 g FOS per day, and more preferably from approximately 150 mg to 5 g of FOS per day, so as to promote the growth of the probiotic Bacillus species over the growth of the pathogenic microbe.

With respect to a therapeutic bath, one embodiment of the present invention provides for the addition and admixing of a composition of dry Bacillus spores (which may additionally contain soaps, oils, fragrances, salts, and the like bath components) to a prepared bath, followed by contacting the infected tissue(s) to the bath water, as by "taking a bath" in the conventional sense. In this embodiment, the therapeutic, probiotic Bacillus spores can be packaged in a system with instructions as described herein. A typical bath would provide from approximately $1 \times 10^8$ to $1 \times 10^{10}$ CFU of bacterial cells or spores per bath, and preferably from approximately $1 \times 10^9$ to $5 \times 10^9$ CFU of bacterial cells or spores per bath.

Specific methods for the treatment of microbial infections will be more fully described in the Specific Examples section, infra, and include, but are not limited to, the treatment of diaper rash, vaginal yeast infection, opportunistic skin infection, meal fungal infection, superficial skin infection, acne, cold sores, genital Herpes lesions, Herpetic Whitlow, shingles, athlete's foot, and the like.

6.2 Therapeutic Systems for Treatment of Microbial Infections

The present invention further discloses a therapeutic system for treating, reducing, and/or controlling microbial infections comprising a container containing a label and a therapeutic composition of the present invention, wherein said label comprises instructions for the use of the therapeutic composition for the treatment of the infection. For example, the therapeutic system can comprise one or more unit dosages of a therapeutic composition of the present invention. Alternatively, the system can contain bulk quantities of the therapeutic composition. The label contains instructions for using the therapeutic composition in either unit dose or in bulk forms as appropriate, and may include information regarding storage of the composition, disease indications, dosages, routes and modes of administration and the like information.

Furthermore, depending upon the particular contemplated use, the system may optionally contain either combined or in separate packages one or more of the following components: FOS, bath salts, soaps and oils (for bathing use), and the like components. One particularly preferred system comprises unit dose packages of Bacillus spores for use in combination with a conventional bath salt or bath soap product, together with instructions for using the Bacillus probiotic in a therapeutic method.

6.3 The Utilization of Emu Oil as a Carrier in Therapeutic Compositions

Several animal-derived lipids have been examined for utilization as "carrying agents", which are used to disperse and facilitate penetration of these therapeutic compositions through the various dermal and cuticular membranes and tissues. However, prior to the disclosure contained herein, there has been little success in finding an agent that is able to penetrate dense cuticular material such as finger/toenails and animal hooves.

Disclosed herein is the use of an animal-derived lipid, Emu oil, as a "carrying agent" to facilitate the dispersion and penetration of the therapeutic compositions of the present invention through the various dermal and cuticular membranes and tissues, and has been demonstrated to markedly increase the efficacy of anti-microbial and anti-fungal therapies. This lipid material is extracted from the Emu (Dromais Novae-Hollandiae), an indigenous bird of Australia and New Zealand. Although Emu oil has been previously described, the uses which are detailed in these documents elaborate only its benefits as an anti-inflammatory agent for arthritis and its uses for cardiovascular health when ingested, which is similar to the use of Omega-3 fish oils to improve high-density lipoprotein (HDL) cholesterol.

Accordingly, both human and animal dermal diseases, caused by bacterial and/or mycotic dermatophytes, can be mitigated or prevented, while concomitantly maintaining dermal and cuticular health, by use of a combination of active agents in a therapeutic composition which includes anti-fungal/anti-bacterial agents (e.g., organic molecules, proteins and carbohydrates and/or bacterial fermentation products) in combination with Emu oil. In a preferred embodiment of the present invention, a therapeutically-effective concentration of Emu oil is combined with the fermentation products of bacteria that have been shown to produce inhibitory metabolites (e.g., *Bacillus coagulans*) and, optionally, with an anti-microbial agent (e.g., an anti-fungal or antibiotic), in a pharmaceutically-acceptable carrier suitable for administration to the dermal and/or cuticular membranes of an animal.

In one embodiment of the bacterial supernatant composition, the bacterial strain is a member of the Lactobacillus genus including, but not limited to: *Lactobacillus acidophilus, Lactobacillus plantarum, Lactobacillus salivarius, Lactobacillus delbrukil, Lactobacillus rhamnosus, Lactobacillus bulgaricus, Lactobacillus gaserli, Lactobacillus jensenii* and *Lactobacillus sporogenes*. In another embodiment, the bacterial strain is a member of the genus Enterococccus, which include, but are not limited to: *Bacillus facium* and *Enterococccus thermophilus*. In another embodiment, the bacterial strain is a member of the Bifidiobacterium genus, which include, but are not limited to: *Bacillus longum, Bacillus infantis, Bacillus bifidus*, and *Bacillus bifidum*. In another embodiment, the bacterial strain is a member of the genus Bacillus, which include, but are not limited to: *Bacillus coagulans, Bacillus thermophilus, Bacillus laterosporus, Bacillus subtilis, Bacillus megaterium, Bacillus licheniformis, Bacillus mycoides, Bacillus pumilus, Bacillus lentus, Bacillus uniflagellatus, Bacillus cereus* and *Bacillus circulans*. In another embodiment the bacterial strain is a member of the genus Pseudomonas, which include, but are not limited to: *Pseudomonas aeruginosa, Pseudomonas putida, Pseudomonas lindbergii, Pseudomonas cepacia, Pseudomonas florescenes*, and Pseudomonas 679–2. In another embodiment of the present, the strain is a member of the genus Sporolactobacillus. In various other embodiments of the present invention, the bacterial strains which are utilized are members of the genus Micromonospora, Sporolactobacillus, Micrococcus, Berkholderia, Rhodococcus and any of the other bacteria which possess the ability to produce a metabolite that has anti-bacterial, anti-mycotic, or anti-viral activity.

In other embodiments of the present invention, the aforementioned bacterial supernatant compositions may be combined with an active anti-microbial agent which is a non-microbially-derived compound. These non-microbially-derived, anti-microbial compound may include, but are not limited to: a quartenary ammonium chloride, an iodine or iodifer compound (e.g., Betadine®), a phenolic compound, an alcohol compound or tincture (e.g., ethanol, isopropyl, and the like). In other embodiments, the non-microbially-derived, anti-microbial compound is a systemic anti-fungal compound, including, but not limited to: Amphotericin B, Dapsone, Fluconazole, Flucytosine, Griseofulvin, Itraconazole, Kietoconazole, or Miconazole KI. In other embodiments, the non-microbially-derived, anti-microbial compound is a topical anti-fungal compound, including, but not limited to: Amphotericin B, Carbol-Fuchsin, Ciclopirox, Clotrimzole, Econazole, Haloprogin, Ketoconazole, Mafenide, Miconazole, Naftifine, Nystatin, Oxiconazole, Silver Sulfadiazine, Sulconazole, Terbinafine, Tioconazole, Tolnafiate, or Undecylenic acid. In other embodiments, the non-microbially-derived, anti-microbial compound is an anti-fungal vaginal compound, including, but not limited to: Butoconazle, Clotrimazole, Econazole, Gentian Violet, Miconazole, Nystatin, Terconazole, or Tioconazole.

Specific methods for the utilization of Emu oil-containing therapeutic compositions will be more fully described in the Specific Examples section, infra.

6.4 Articles of Manufacture

The present invention also discloses various articles of manufacture which utilize the beneficial aspects of the present invention by combination of the therapeutic composition with various medical or personal hygiene devices so as to reduce or prevent microbial infections associated with the use of these devices. The invention comprises compositions of a Bacillus and/or isolated *Bacillus coagulans* active agent applied to a solid surface or impregnated into a solid matrix of any device or article of manufacture that is intended to be in contact with skin or a mucous membrane. Preferably the solid surface is a flexible article than can be worn on or wiped on the skin or mucous membrane. More preferably, when the flexible item carrying the Bacillus and/or the isolated active agent is to be worn on the skin it includes a means for attaching the article to the skin such as, for example, an adhesive layer, inter-engaging hook and pile (i.e., Velcro®) connectors, or other well-known means of attachment such as ties, snap closures, elastic, buttons and the like.

Specific embodiments which include a Bacillus and/or isolated *Bacillus coagulans* active agent are diapers, towelettes (e.g, baby wipes or feminine hygiene towelettes), tampons, dermal patches, adhesive tape, absorbent pads, articles of clothing (e.g., underclothes, sleeping apparel), bath towels, wash cloths, and the like. The article may be made of fibrous woven, knitted or non-woven materials, occlusive or non-exclusive films or membranes, synthetic polymer fibers, films, membranes and foams (e.g, nylon, polytetrafluoroethylene (PTFE, such as Teflon® or Gore-Tex®), polystyrene, polycarbonate, polyvinylchioride and polysulphone). All of these forms are well-known within the art and include, for example, knitted or woven fabrics, non-woven fabrics such as felt and batting, fiber balls of cotton, rayon, cellulose or synthetic fibers and the like materials.

The Bacillus and/or *Bacillus coagulans* isolated active agent can be applied to the solid surface using any of a variety of known methods including, for example, applying a powder, spray drying the probiotic onto the material or soaking the material in a solution containing the probiotic and then using the wetted material or drying the material prior to use. Porous material may contain the Bacillus and/or the isolated active agent in the pores or interstices of the solid material. The Bacillus and/or the isolated active agent can be attached by adhesion, such as by attachment to an adhesive layer that is then applied to the skin (e.g., in a bandage or dermal patch). The Bacillus and/or the isolated active agent can be impregnated into the solid material during the manufacturing process of the flexible article (e.g., added to a synthetic composition before or during the polymerization process). The pressure and heat resistance of Bacillus spores makes them particularly suitable for incorporation into the material during manufacturing. Any of the solid materials carrying Bacillus and/or the isolated active agent can also be packaged individually or in groups, suitable for holding the treated material using standard packaging materials (e.g., in a shrink wrapper, sealed packet, protective wrapper or dispensing container suitable for holding dry or wet materials). The article of manufacture can have applied thereon any of the additional/optional components of a therapeutic composition of this invention, including carriers, salts, FOS, fragrances, and the like.

Any of a variety of methods for placing the therapeutic composition onto a subject article can be used, and therefore the invention need not be so limited. However, preferred methods include a "spray-dry" method in which the material is exposed in a low humidity chamber to an atomized mix containing a liquid composition, where the chamber is subsequently exposed to approximately 80–110° F. to dry the liquid, thereby impregnating the material of the article with the components of the composition.

A typical concentration is from approximately $1 \times 10^5$ to $1 \times 10^9$ CFU of viable bacterium or spores/in$^2$ of external surface of fibrous carrier/article material. Following drying, the article is ready for storage in a sterile package, or for direct use.

7. Specific Examples

The following examples relating to the present invention are illustrative and should not be construed as specifically limiting the invention. Moreover, such variations of the invention, now known or later developed, which would be within the purview of one skilled in the art are to be considered to fall within the scope of the present invention hereinafter claimed.

7.1 Probiotic *Bacillus coagulans* Activity (A) Anti-Mycotic Probiotic Activity of *Bacillus coagulans*

The ability of *Bacillus coagulans* to inhibit various fimgal pathogens was demonstrated using an in vitro assay. In the assay, potato-dextrose plates (DIFCO®, Detroit, Mich.) were prepared using standard procedures and were inoculated individually with a confluent bed (about $1.7 \times 10^6$) of various species of the fingus Trichophyton. The tested fingal strains of Trichophyton species (available from the American Type Culture Collection (ATCC; Manassas, Va.)) and their ATCC accession numbers, as well as the results of in vitro inhibition by *Bacillus coagulans* are illustrated in FIG. 3.

Inhibition by *Bacillus coagulans* was ascertained by placing on the plate approximately $1.5 \times 10^6$ colony forming units (CFU) in 10 µl of broth or buffer, plated directly in the center of the potato-dextrose plate, with one test locus per plate. The size of each test locus was approximately 8 mm in diameter and a minimum of three tests were performed for each inhibition assay. The negative control consisted of a 10 ml volume of sterile saline solution, whereas the positive control consisted of a 10 ml volume 2% Miconazole (1-[2-(2,4-dichlorophenyl)-2-[(2,4-dichlorophenyl) methoxylmethyl-1, 11-imidazole within an inert cream.

The plates were then incubated for approximately 18 hr at 30° C., at which time the zones of inhibition were measured. As designated herein, "excellent inhibition" means the zone was 10 mm or greater in diameter; and "good inhibition" means the zone was greater than 2 mm in diameter, but less than 10 mm in diameter.

The results of the in vitro inhibition by *Bacillus coagulans* is illustrated in FIG. 3. For each of the Trichophyton species tested, the disease condition associated with an infection is indicated in column 2 of FIG. 3. For comparison, no zone of inhibition was seen with the negative control, whereas good inhibition (approximately 8.5 mm diameter, mean average of three tests) was seen with the positive control.

Similarly, the ability of *Bacillus coagulans* to inhibit various yeast pathogens was demonstrated in vitro for four species of Candida, all of which are available from the American Type Culture Collection (ATCC; Manassas, Va.). Each of the yeast pathogens and their ATCC accession numbers are illustrated in FIG. 4.

In the in vitro inhibition assay, potato-dextrose plates (DIFCO®, Detroit, Mich.) were prepared using standard procedures and were inoculated individually with a confluent bed about $1.7 \times 10^6$ of the four species of Candida. Inhibition by *Bacillus coagulans* was tested by placing on the plate about $1.5 \times 10^6$ colony forming units (CFU) in 10 µl of broth or buffer, plated directly in the center of the potato-dextrose plate with one test locus of about 8 mm in diameter per plate. A minimum of three. tests were performed for each inhibition assay. The negative control consisted of a 10 µl volume of a sterile saline solution, whereas the positive control consisted of a 1 µl volume of Miconazole cream.

The plates were then incubated for approximately 18 hr at 30° C., at which time the zones of inhibition were measured. As designated herein, "excellent inhibition" means the zone was 10 mm or greater in diameter; and "good inhibition" means the zone was greater than 2 mm in diameter, but less than 10 mm in diameter.

The results of the in vitro tests are shown in FIG. 4 with the pathological conditions in humans associated with infection by the Candida species shown in column 2. As expected, no inhibition was seen with the negative control and good inhibition (approximately 8.7 mm diameter; average of three tests) was seen with the positive control.

(C) Anti-Microbial Probiotic Activity of *Bacillus coagulans*

The ability of *Bacillus coagulans* to inhibit various opportunistic bacterial pathogens was quantitatively ascertained by use of an in vitro assay. This assay is part of a standardized bacterial pathogen screen (developed by the U.S. Food and Drug Administration(FDA)) and is commercially available on solid support disks (DIFCO® BACTROL® Disk Set). To perform the assay, potato-dextrose plates (DIFCO®) were initially prepared using standard procedures. The plates were then individually inoculated with each of the bacteria (approximately $1.5 \times 10^6$ CFU) to be tested, so as to form a confluent bacterial bed.

Inhibition by *Bacillus coagulans* was subsequently ascertained by placing approximately $1.5 \times 10^6$ CFU of *Bacillus coagulans* in 10 µl of broth or buffer, directly in the center of the potato-dextrose plate, with one test locus being approximately 8 mm in diameter per plate. A minimum of three test loci were used for each assay. The negative control consisted of a 10 µl volume of a sterile saline solution, whereas the positive control consisted of a 10 µl volume of glutaraldehyde. The plates were then incubated for approximately about 18 hr at 30° C., at which time the zones of inhibition were measured. As designated herein, "excellent inhibition" means the zone was 10 mm or greater in diameter; and "good inhibition" means the zone was greater than 2 mm in diameter but less than 10 mm in diameter.

As expected, no "inhibition" was seen with the negative, saline control, and excellent "inhibition" (approximately 16.2 mm diameter; average of three tests) was seen with the positive, glutaraldehyde control. For the enteric microorganisms tested, the following inhibition by *Bacillus coagulans* was found: (i) Clostridium species—excellent inhibition; (ii) *Escherichia coli*—excellent inhibition; (iii) Clostridium species—excellent inhibition, where the zone of inhibition was consistently greater than 15 mm in diameter. Similarly, excellent inhibition was also seen for the opportunistic pathogens *Pseudornonas aeruginosa*, and *Staphylococcus aereus*.

In summation, pathogenic enteric bacteria which were shown to be inhibited by *Bacillus coagulans* activity include, but are not limited to: *Staphylococcus aureus; Staphylococcus epidermidus; Streptococcus pyogenes; Pseudomonas aeruginosa; Escherichia coli*(enterohemorragic species); numerous Clostridium species (e.g., *Clostridium perfingens, Clostridium botulinum, Clostridium tributrycum, Clostridium sporogenes*, and the like); *Gardnereia vaginails; Proponbacterium aenes; Aeromonas hydrophia*; Aspergillus species; Proteus species; and Klebsiella species.

7.2 Therapeutic Composition Formulations

(A) Formulation 1: Bathing Formulation (per bath/dosage)

| | |
|---|---|
| *Bacillus coagulans* | $2.5 \times 10^8$ spores (approximately 18 mg) |
| Bath salts (sea & mineral salts) | 10 gm |
| Fructo-oligosaccharides (FOS) | 1 gm |
| Micro-crystalline cellulose (MCC) | 5 gm |
| Fragrance | Trace |

(B) Formulation 2: Topical Ointment (per ml)

| | |
|---|---|
| *Bacillus coagulans* extract | 100 µl (see Specific Example C(ii)) |
| Lanolin | 780 µl |
| Emu oil | 100 µl |
| Geranium essential oil | 20 µl |
| Fragrance | Trace |

(C) Formulation 3: Topical Liquid for Dropper Application (per ml)

| | |
|---|---|
| *Bacillus coagulans* extract | 500 µl (see Specific Example c(ii)) |
| Emu oil | 450 µl |
| Geranium essential oil | 20 µl |
| Tween-80 detergent | 30 µl |
| Fragrance | Trace |

(D) Formulation 4: Powder (per gram)

| | |
|---|---|
| *Bacillus coagulans* | $1 \times 10^8$ spores (approximately 8 mg) |
| Talc | 992 mg |
| Powdered lavender fragrance | Trace |

7.3 Growth of *Bacillus coagulans*

*Bacillus coagulans* is aerobic and facultative, grown typically in nutrient broth, pH 5.7 to 6.8, containing up to 2% (wt/vol) NaCl, although neither NaCl nor KCl are an absolute requirement for growth. A pH value ranging from approximately pH 4 to pH 6 is optimum for initiation of sporulation. It is optimally grown at about 30° C. to about 55° C., and the spores can withstand pasteurization. It exhibits facultative and heterotrophic growth by utilizing a nitrate or sulfate source.

*Bacillus coagulans* can be grown in a variety of media, although it has been found that certain growth conditions produce a culture which yields a high level of sporulation. For example, sporulation is enhanced if the culture medium includes 10 mg/liter of manganese sulfate, yielding a ratio of spores to vegetative cells of about 80:20. In addition, certain growth-conditions produce a bacterial spore which contains a spectrum of metabolic enzymes particularly suited for the present invention (i.e., the control of microbial infections). Although spores produced by these particular growth conditions are preferred, spores produced by any compatible growth conditions are suitable for producing a *Bacillus coagulans* useful in the present invention.

(A) Culture of Vegetative *Bacillus coagulans*

*Bacillus coagulans* is aerobic and facultative, and is typically cultured at pH 5.7 to 6.8, in a nutrient broth containing up to 2% (by wt) NaCl, although neither NaCl, nor KCl are required for growth. A pH of about 4.0 to about 7.5 is optimum for initiation of sporulation (i.e., the formation of spores). The bacteria are optimally grown at 30° C. to 45° C., and the spores can withstand pasteurization. Additionally, the bacteria exhibit facultative and heterotrophic growth by utilizing a nitrate or sulfate source.

*Bacillus coagulans* can be cultured in a variety of media, although it has been demonstrated that certain growth conditions are more efficacious at producing a culture which yields a high level of sporulation. For example, sporulation is demonstrated to be enhanced if the culture medium includes 10 mg/l of $MgSO_4$ sulfate, yielding a ratio of spores to vegetative cells of approximately 80:20. In addition, certain culture conditions produce a bacterial spore which contains a spectrum of metabolic enzymes particularly suited for the present invention (i.e., production of lactic acid and enzymes for the enhanced probiotic activity and biodegradation). Although the spores produced by these aforementioned culture conditions are preferred, various other compatible culture conditions which produce viable *Bacillus coagulans* spores may be utilized in the practice of the present invention.

Suitable media for the culture of *Bacillus coagulans* include: PDB (potato dextrose broth); TSB (tryptic soy broth); and NB (nutrient broth), which are all well-known within the field and available from a variety of sources. In one embodiment of the present invention, media supplements which contain enzymatic digests of poultry and/or fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Newark, N.J.); BBL (Cockeyesville, Md.); Advanced Microbial Systems (Shakopee, Minn.); and Troy Biologicals (Troy, Md.

In a preferred embodiment of the present invention, a culture of *Bacillus coagulans* Hammer bacteria (ATCC No. 31284) was inoculated and grown to a cell density of approximately $1 \times 10^8$ to $1 \times 10^9$ cells/ml in nutrient broth containing: 5.0 g Peptone; 3.0 g Meat Extract; 10–30 mg $MnSO_4$ and 1,000 ml distilled water, the broth was then adjusted to pH 7.0. The bacteria were cultured by utilization of a standard airlift fermentation vessel at 30° C. The range of $MnSO_4$ acceptable for sporulation was found to be 1.0 mg/l to 1.0 g/l. The vegetative bacterial cells can actively reproduce up to 65° C., and the spores are stable up to 90° C.

Following culture, the *Bacillus coagulans* Hammer bacterial cells or spores were collected using standard methods (e.g., filtration, centrifugation) and the collected cells and spores may subsequently be lyophilized, spray dried, air dried or frozen. As described herein, the supernatant from the cell culture can be collected and used as an extracellular agent secreted by *Bacillus coagulans* which possesses antimicrobial activity useful in a formulation of this invention.

A typical yield obtained from the aforementioned culture methodology is in the range of approximately $10^9$–$10^{13}$ viable spores and, more typically, approximately $10$–$15 \times 10^{10}$ cells/spores per gram prior to being dried. It should also be noted that the *Bacillus coagulans* spores, following a drying step, maintain at least 90% viability for up to 7 years when stored at room temperature. Hence, the effective shelf-life of a composition containing *Bacillus coagulans* Hammer spores at room temperature is approximately 10 years.

(B) Preparation of *Bacillus coagulans* Spores

A culture of dried *Bacillus coagulans* Hammer bacteria (ATCC No. 31284) spores may be prepared as follows. Approximately $1 \times 10^7$ spores were inoculated into one liter of culture medium containing: 24 g (wt./vol.) potato dextrose broth; 10 g of an enzymatic-digest of poultry and fish tissue; 5 g of fructo-oligosaccharides (FOS); and 10 g $MnSO_4$. The culture was maintained for 72 hours under a high oxygen environment at 37° C. so as to produce a culture having approximately $15 \times 10^{10}$ cells/gram of culture. The culture was then filtered to remove the liquid culture medium and the resulting bacterial pellet was resuspended in water and lyophilized. The lyophilized bacteria were ground to a fine "powder" by use of standard good manufacturing practice (GMP) methodologies. The powder is then combined into Formulation 1 or Formulation 4 as described in Specific Example B to form dry powder compositions.

It should also be noted that the most preferred embodiments of the present invention utilizes *Bacillus coagulans* in spore, rather than vegetative bacterial form.

7.4 Preparation of *B. coagulans* and *P. lindbergii* Extracellular Products

One liter cultures of either *Bacillus coagulans* or *Pseudomonas lindbergii* were prepared as described in Example C(i), except that the fructo-oligosaccharide (FOS) was omitted. The culture was maintained for 5 days as described, at which time FOS was added at a concentration of 5 g/liter, and the culture was continued. Subsequently, 20 ml of carrot pulp was then added at day 7, and the culture was harvested when the culture became saturated (i.e., no substantial cell division).

The culture was first autoclaved for 30 minutes at 250° F., and then centrifuged at 4000 r.p.m. for 15 mm. The resulting supernatant was collected and filtered in a Buchner funnel through a 0.8 $\mu$m filter. The filtrate was collected and further filtered through a 0.2 $\mu$m Nalge vacuum filter. The resulting final filtrate was then collected (an approximate volume of 900 ml) to form a liquid containing an extracellular product which was to be quantitatively analyzed and utilized in the subsequent inhibition studies.

The following methodologies were utilized to characterize the supernatant. Liquid Chromatography of Proteins: 20 ml of culture supernatant was loaded on an analytical Mono 9 chromatography column (Pharmacia) equilibrated in Buffer A (0.25 M Tris HCl; pH 8.0) using a BioCAD Sprint chromatography system (Perspective Biosystems, Inc.) running at 2 ml/mm. The column was washed with 15 ml of Buffer A and eluted with a linear gradient ranging from 0% B (i.e., Buffer B is an aqueous 3 M NaCl solution) to 40% B, over a time frame of 12 minutes. The column was then washed with 100% B for 5 minutes. Subsequently, the column was re-equilibrated with Buffer A. Absorbance was monitored at 280 nm to detect elution of aromatic amino acids (i.e., Tyrosine) found in bacterial proteins.

The results demonstrate a mixture of proteins, the majority of which elute at 0.1 M to 0.8 M NaCl, and a minor fraction of material which elutes at a 3.0 M NaCl concentration. Fractions were collected and saved, and dialyzed in Spectrapor dialysis membranes (MW "cut-off" approximately 1,000 Daltons) against water, to facilitate subsequent analysis.

Ultraviolet and Visible Spectroscopy: Differential absorbance spectra were determined between 200 and 600 nm wavelengths in 1 cm quartz cuvettes using a Uvikon 930 scanning spectrophotometer (Kontron Instruments). The baseline was determined with water or LB broth culture media (DIFCO).

Figure 5B:
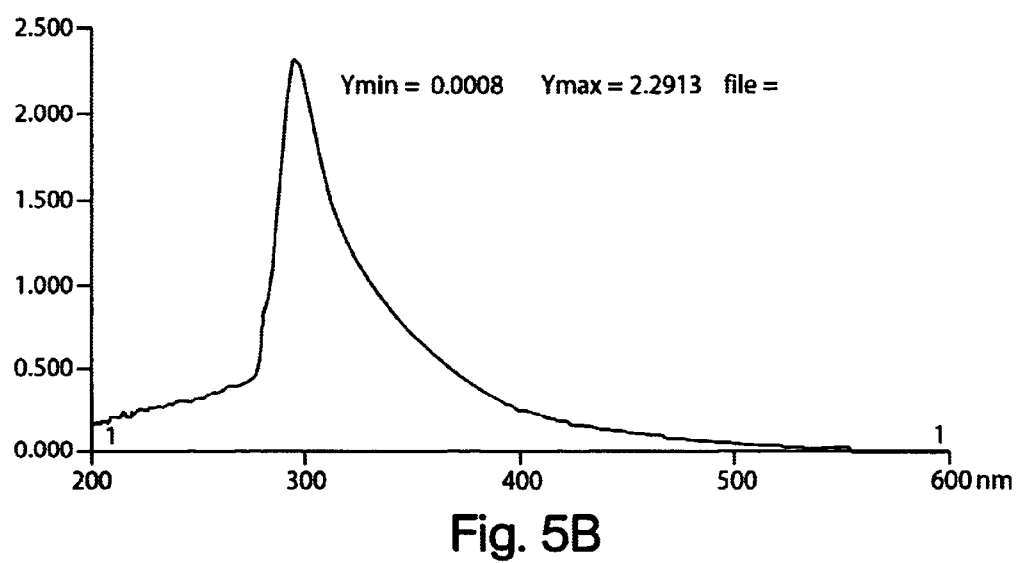
Figure 6A:
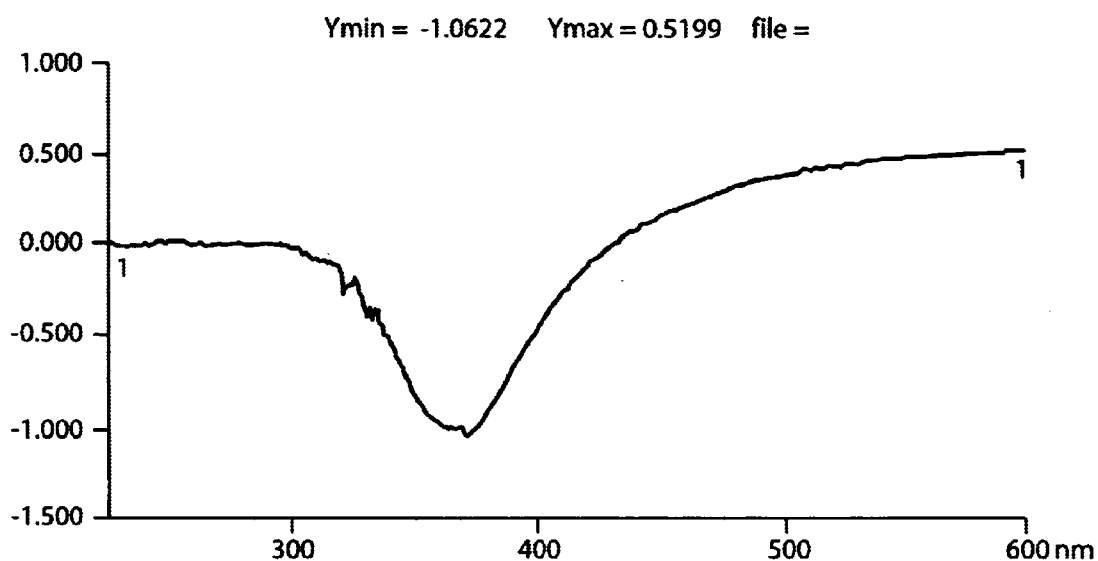
FIG. 6: illustrates a wavelength scan of *Bacillus coagulans* (Panel A) and *Pseudomonas lindbergii* (Panel B) supernatants with an LB broth blank.
Figure 6B:
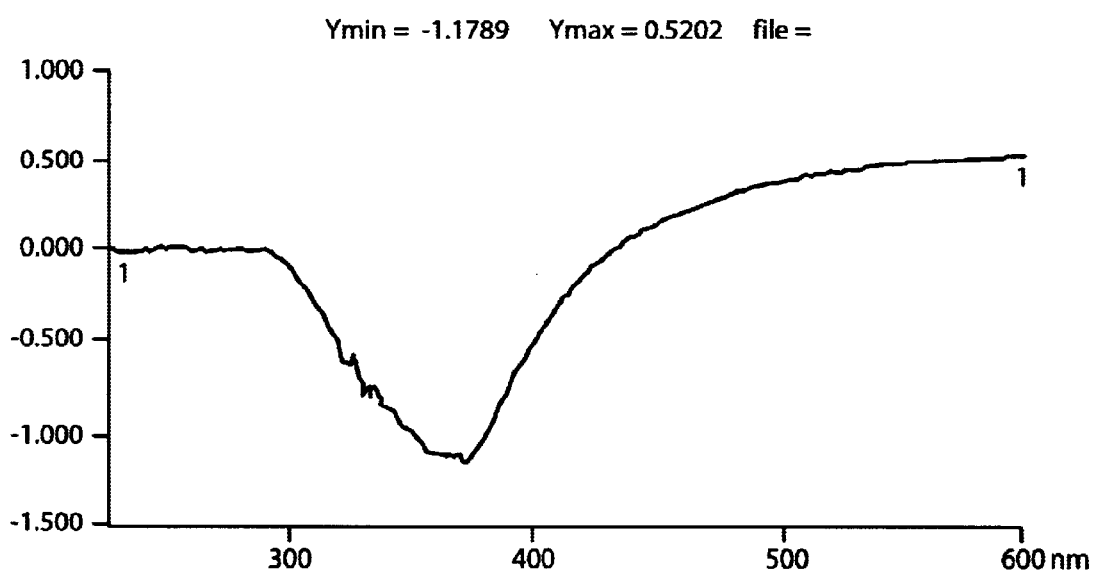

The results with a water blank show an absorbance peak at 290 nm to 305 nm for Bacillus coagulans (see FIG. 5; Panel A) and *Pseudomonas lindbergii* (see FIG. 5; Panel B), with a significant amount of additional absorbing material found between 210 nm and 400 nm. There was also demonstrated to be significant absorbance in the UV wavelengths, primarily due to presense of protein. The results with LB broth (see FIG. 6) show a marked diminution of absorbing material in the 300 nm to 440 nm range, but an increase in the higher wavelengths, thus denoting an increase in the highly-conjugated organics (i.e., proteins) with a consumption of simpler ones (i.e., amino acids). The fact that there is little change at the wavelengths where proteins specifically absorb is due to the fact that LB already contains 10 grams of casein hydrolysate (Casainino acids, DIFCO).

Figure 7:
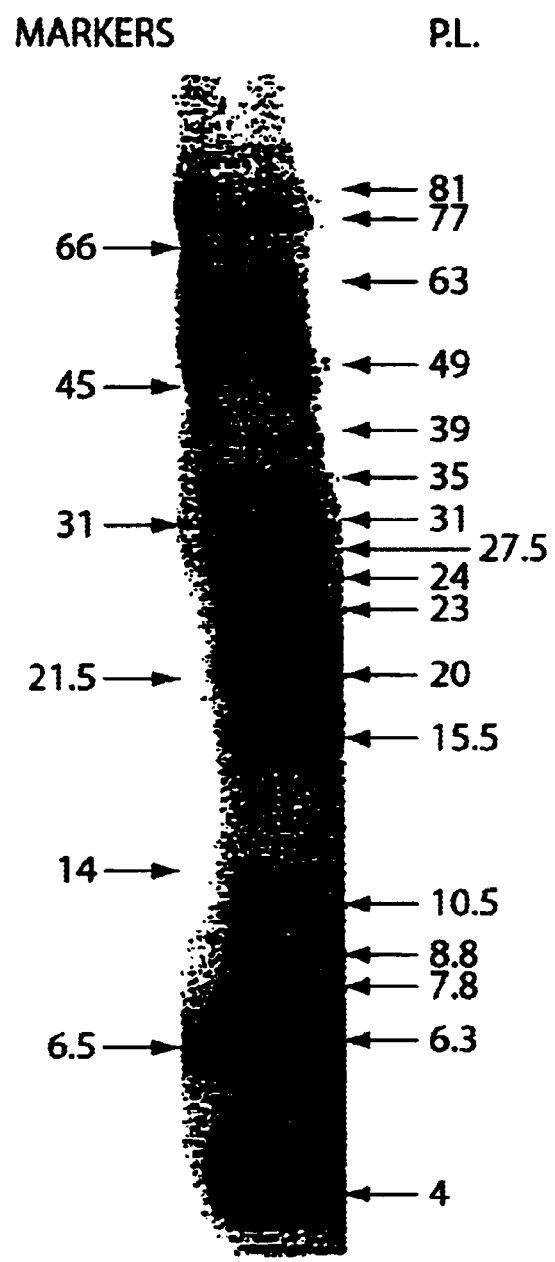
FIG. 7: illustrates a 12% acrylamide SDS PAGE of *Pseudomonas lindbergii* proteins. The left lane are molecular weight markers.
Figure 8:
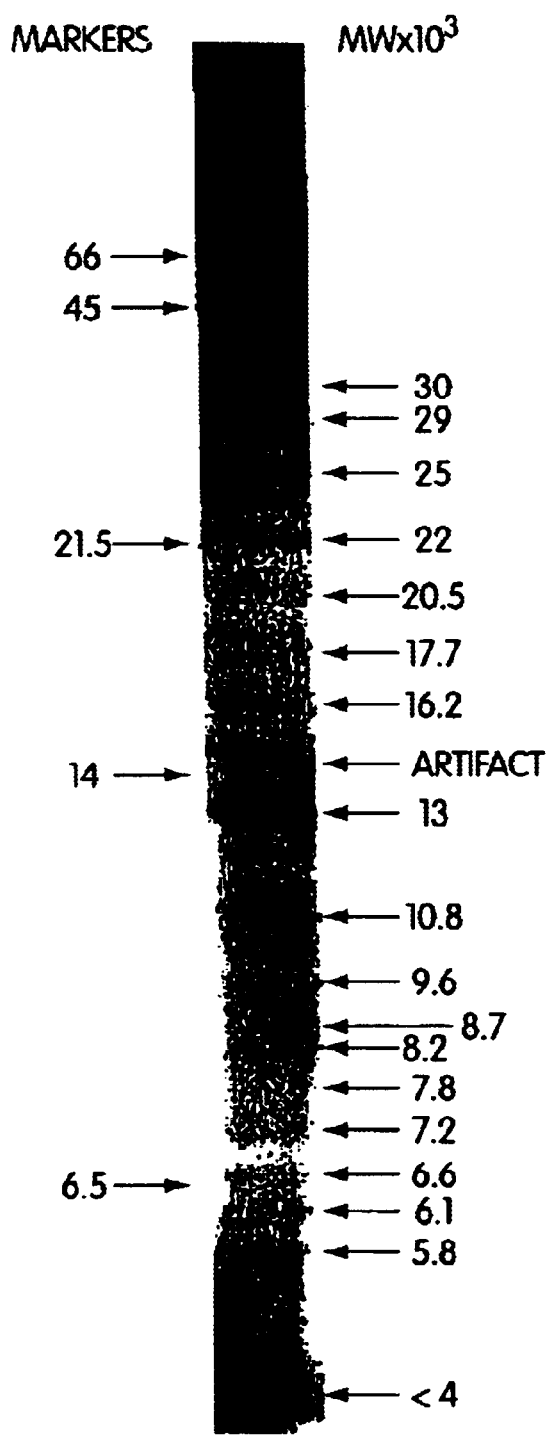
FIG. 8: illustrates a 12% acrylamide SDS PAGE of *Bacillus coagulans* proteins. The left lane are molecular weight markers.

SDS Polyacrylainide Gel Electrophoresis: Electrophoresis was performed by the method of Laemmli (see Laemmli, 1970. *Nature* 227: 680–685) and the acrylamide gels were poured in 1 mm cassettes (Novex) and run according to recommendations of the commercial supplier (i.e., 120 volts, for 90 minutes [12% gel] and for 2 hours [16%]). The gels were then silver stained by the method of Blum, et al. (see Blum, et al., 1987. Electrophoresis 8: 93–99). A 12% acrylamide gel was found to best resolved the *Pseudomonas lindbergii* proteins (see FIG. 7); whereas a 16% gel best resolved the *Bacillus coagulans* proteins (see FIG. 8). All samples were dialyzed against water prior to preparation for electrophoresis so as to ameliorate salt-associated electrophoretic artifacts. Wide range protein markers (BioRad) were used for protein molecular weight determination.

The electrophoretic results demonstrated a significant number of proteinaceous bands in the less-than 4,000 to 90,000 Dalton range for *Pseudomonas lindbergii* and in the less-than 4,000 to 30,000 Dalton range for *Bacillus coagulans*.

High Pressure Liquid Chromatography: Five ml of culture supernatants were extracted with 2 ml of acetonitrile, benzene, or 24:1(v:v) chloroform:isoamyl alcohol for approximately two hours. The phases were allowed to separate for four hours and further separated by centrifugation at 5,000×g for 10 minutes. The organic phase was then filtered through 0.2 μm PVDF filters (Gehnan Acrodisc LC-13) and loaded on an Econosil C-18 10U HPLC column (Altech) in a mobile phase of 20 mM Tris-HCl (pH 7.5). Elution was started after a total of 5 minutes, in a 15 minute linear gradient to 60% acetonitrile (ACN) in water. Elution was continued for 5 minutes in 60% ACN, and the column was then washed and re-equilibrated in 20 mM Tris-HCl (pH 7.5).

Figure 9:
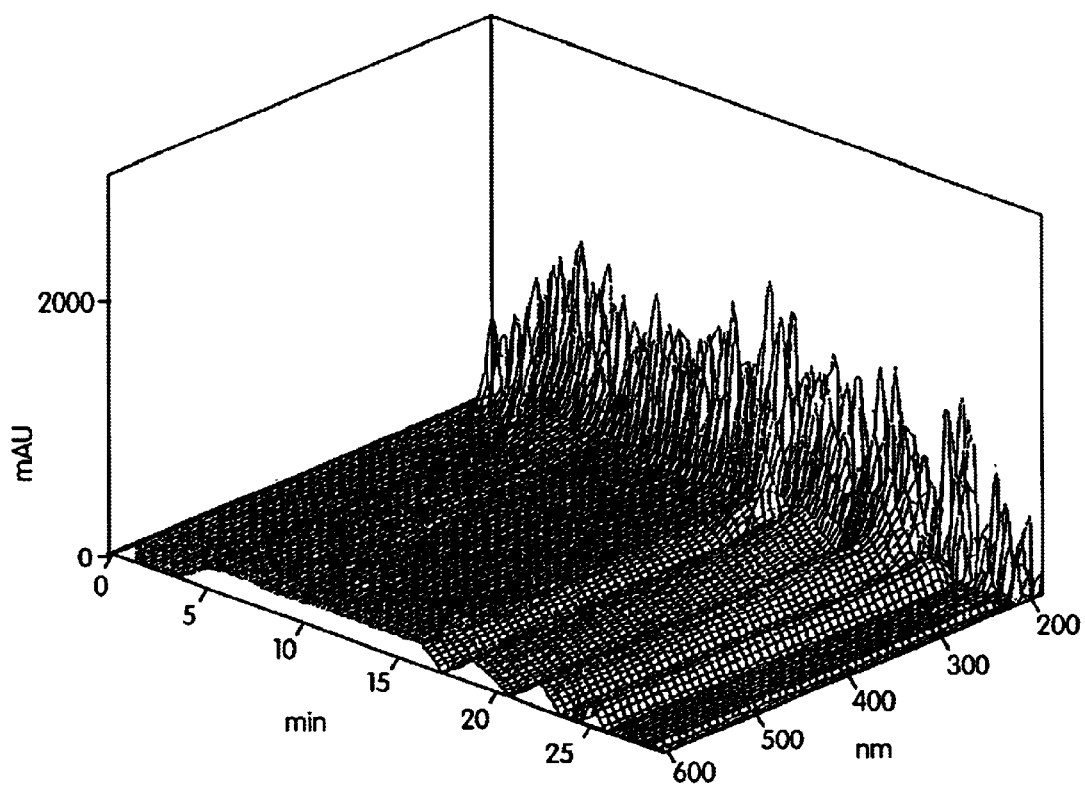
FIG. 9: illustrates a reverse-phase HPLC of acetonitrile-extracted *Pseudomonas lindbergii* supernatant.
Figure 10:
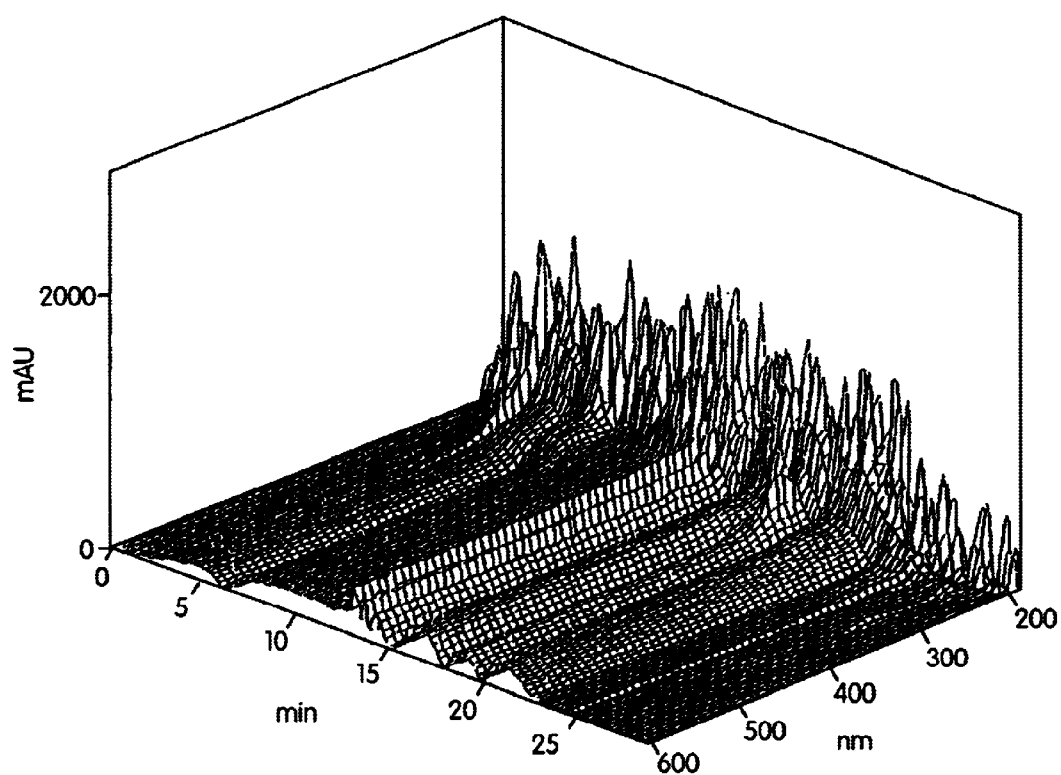
FIG. 10: illustrates a reverse-phase HPLC of acetonitrile-extracted *Bacillus coagulans* supernatant.

The results of reverse-phase HPLC of ACN-extracted *Bacillus coagulans* and *Pseudomonas lindbergii* are illustrated in FIG. 9 and FIG. 10, respectively, and demonstrate that increasing the organic character of the solvent led to increasingly "organic profiles" in the HPLC (i.e., an increase in material eluting at higher percentage of ACN) and an increase in the capture of pigmented molecules (i.e., molecules which absorb visible light). These aforementioned molecules will be isolated and further characterized.

The results of these aforementioned analytical methodologies demonstrated that the culture supernatants from both *Bacillus coagulans* and *Pseudomonas lindbergii* are very heterogeneous in nature, containing a plurality of proteinaceous and organic molecules. However, the molecules which predominate are the proteins, of which there are a total of 20 distinct species in each of the samples. These protein species can be further fractionated by use of ion exchange chromatography, thus allowing additional characterization. Furthermore, there are also numerous pigmented molecules (i.e., molecules which absorb visible light) that are both highly conjugated (based upon their absorbance at high wavelengths) and hydrophobic (based upon their preference for non-polar solvents and retention on the C-18 HPLC column).

Following the aforementioned analysis and characterization, the assay initially described in Specific Example A(i) utilizing *Candida albicans*, 1 ml of the aforementioned extracellular product was added to the test plate in place of the bacterium. After an identical culture time, a zone of inhibition of approximately 10 to 25 mm in diameter was observed. These results illustrate the potent antimicrobial activity of the *Bacillus coagulans* extracellular product, which is of "excellent" quality using the terminology set forth in Specific Examples A(i)–(iii).

In an additional assay, a comparison of the anti-mycotic, Fluconazole with *Bacillus coagulans* supernatant in the inhibition of various bacterial, fungal, and yeast species, was performed. As illustrated in FIG. 11, these supernatants were effective in inhibiting a majority of the organisms against which they were tested. Serial dilutions of the *Bacillus coagulans* supernatant were performed with RPMI medium and inhibition was determined at 80% in accordance with the NCCLS standard for anti-fungal susceptibility.

Specifically, the results demonstrated that *T. rubrum* was totally inhibited by undiluted supernatant, and 1:2, 1:4, 1:8, 1:16, 1:32, 1:64, 1:128, and 1:256 serial dilutions, and the organism was 80% inhibited by the compound diluted 1:512 with RPMI medium. *T. mentagrophytes* was totally inhibited by the undiluted supernatant, and 1:2, 1:4, 1:8, and 1:16 serial dilutions, and the organism was 80% inhibited by the supernatant diluted 1:32 with RPMI medium. *C. parapsilosis* was totally inhibited by the undiluted supernatant and 1:2, 1:4, 1:8, 1:16, 1:32, 1:64, 1:128, and 1:256 serial dilutions, and the organism was 80% inhibited by the supernatant diluted 1:16 with RPMI medium. *C. albicans* was totally inhibited by the undiluted supernatant and a 1:2 dilution, and the organism was 80% inhibited by the supernatant diluted 1:4 with RPMI medium. Acremonium sp. was totally inhibited by the undiluted supernatant and was 80% inhibited by the supernatant diluted 1:2 with RPMI medium. Scopulariopis sp. was 80% inhibited by the undiluted supernatant, but was uninhibited by any of the serial dilutions of the supernatant. The supernatant showed no inhibitory activity against *C. glabrata, C. krusel*, or the two Aspergillus species. Thus, the supernatant was demonstrated to possess marked inhibitory activity, in a wide variety of dilutions, against a majority of the tested organisms. Moreover, the *Bacillus coagulans* supernatant appeared to be extremely effective against dermatophytes (e.g., Trichophyton sp.), which are a causative organism in many mammalian dermal diseases.

In a preferred embodiment of the present invention, the liquid containing the extracellular product was formulated into a liquid ointment composition for use in direct application onto a tissue using a dropper, such as would be convenient to treat a fungal infection of the toe nail. This liquid ointment was prepared by combining the liquid extracellular product produced above with Emu essential oil in a ratio of approximately 8:2, and trace fragrances were added to produce an aesthetic component.

Alternatively, one may use any liposomal or oil based transdermal delivery component in place of the Emu oil. The typical ratio of probiotic extracellular product to carrier or delivery component is a range of from approximately 1% to 90% probiotic, and preferably is approximately 10% to 75% probiotic.

7.5 Topical Application to Prevent Diaper Rash

A powder, aerosol spray liquid, or aerosol spray powder containing *Bacillus coagulans* active agent, preferably *Bacillus coagulans* spores, is applied to diapers by the consumer before use. Alternatively, disposable diapers supplied from the manufacture may contain *Bacillus coagulans* active agent, preferably *Bacillus coagulans* spores, impregnated into the diaper material where it would be adjacent to the child's skin when in use. When the diaper becomes wetted by urine and/or fecal material, the spores are activated, usually within about twenty minutes. *Bacillus coagulans* spore germination and *Bacillus coagulans* growth after spore germination produce sufficient anti-fungal, including anti-yeast, activity to inhibit growth of yeast and fungal organisms in the diapers and on the child's skim thus preventing diaper rash or other diaper-associated opportunistic infections.

Alternatively or in addition toreating diapers with *Bacillus coagulans*, the child's skin in the diaper area can be treated with a saturated soft cloth wipe, powder, aerosol spray liquid, aerosol spray powder, lotion, cream or ointment containing *Bacillus coagulans* active agent. Preferably, the *Bacillus coagulans* formulation is applied to the child's skin after bathing and/or when the diapers are changed.

Suitable formulations include a powder of talc and optionally fragrance 10 containing approximately $1\times10^5$ to $1\times10^{10}$ *Bacillus coagulans* spores per gram. Other suitable powder formulations contains talc, mineral oil, magnesium carbonate, DMDM, hydantoin, and approximately $1\times10^5$ to $1\times10^{10}$ *Bacillus coagulans* spores per gram of a corn starch and calcium carbonate powder. An aerosol powder that includes an isobutane or other well known propellant made using standard methods is also suitable. An aerosol spray may be formulated by combining approximately $1\times10^6$ to $1\times10^{11}$ *Bacillus coagulans* spores per gram in isopropyl myristate, about 60% (w/w) SD alcohol 40-B, and isobutane as the propellant using standard methods. A manual pump spray containing $1\times10^6$ to $1\times10^{11}$ *Bacillus coagulans* spores per gram of a neutral aqueous solution with no chemical propellant is also suitable. A suitable spray formulation includes alcohol, glycerin, purified water and methylparaben in addition to the *Bacillus coagulans* probiotic. A cream formulation includes aloe vera gel, isopropyl myristate, methylparaben, polysorbate 60, propylparaben, purified water, sorbitan monostearate, sorbitol solution, stearic acid and approximately $1\times10^5$ to $1\times10^{10}$ *Bacillus coagulans* spores per gram. Another protective cream contains vitamins A and D equivalent to the concentration found in cod liver oil, cetylpalmitate, cotton seed oil, glycerin, glycerol monostearate, optional fragrance, methylparaben, mineral oil, potassium stearate, propylparaben and approximately $1\times10^5$ to $1\times10^{10}$ *Bacillus coagulans* spores per gram. An ointment contains cod liver oil, lanolin oil, methylparaben, propylparaben, talc, optional fragrance and approximately $1\times10^5$ to $1\times10^{10}$ *Bacillus coagulans* spores per gram. Another ointment formulation includes petrolatum, water, paraffin, propylene glycol, milk protein, cod liver oil, aloe vera gel, optional fragrance, potassium hydroxide, methyl paraben, propyl paraben, vitamins A, D and E and approximately $1\times10^5$ to $1\times10^{10}$ *Bacillus coagulans* spores per gram. A soft cloth pad (i.e., a baby wipe) is soaked in an aqueous solution (e.g., water, amphoteric 2, aloe vera gel, DMDM, hydantoin or an aqueous solution of 30% to 70% alcohol) and approximately $1\times10^5$ to $1\times10^{10}$ *Bacillus coagulans* spores per gram.

7.6 Topical Treatment of Vaginal Yeast Infection (A) Vaginal Microecology

It is commonly known to those individuals skilled within the relevant arts that lactic acid-producing microorganisms (e.g., Lactobacillus) play an important role in the maintenance of a healthy vaginal ecology. However, the traditional methodologies utilized for the administration of these biorational materials do not address the numerous modes of infection of Candida and Gardnerella species, which can cause serious disease.

The vast majority of gynecologists are adamant regarding the risks of vaginal infections as a result of frequent bathing. Accordingly, gynecologists recommend the use of showers, rather than immersion bathing, to mitigate the probability of developing subsequent vaginal infections due to the associated disturbances of the "normal," lactic acid-producing vaginal flora.

(B) Yeast-Mediated Vaginal Infections

Yeast infections or vuvo-vaginal candidaiasis (VVC) is caused by various species of Candida (e.g., primarily *Candida albicans*). Over 85% of all women, at one time or another, suffer from vuvo-vaginal candidaiasis. For example, the market within the United States market for anti-fungal compounds which may be administered to ameliorate this disease is over $700 million dollars per year, with an associated 9–11% growth rate per annum. Moreover, each year, additional strains of these aforementioned mycotic pathogens are becoming resistant to the commonly utilized anti-fungal compounds (e.g., Ketoconazole, Miconazole, Fluconazole, and the like).

Healthy vaginal ecology is primarily dependant upon specific, indigenous lactic acid-producing microorganisms (e.g., Lactobacilli). Hence, there have been numerous attempts within the prior art to develop products and/or methodologies which will augment or re-establish these lactic acid-producing bacteria. For example, one product attempted to utilize hydrogen peroxide- ($H_2O_2$) producing Lactobacilli as a vaginal suppository therapy for the amelioration of vaginal yeast infections.

Viability of the microorganisms continues to be the main difficulty in the use of Lactobacilli for vaginal supplementation, although it has been suggested by many companies that market Lactobacilli vaginal suppositories that any hardy bacterial strain is sufficient to accomplish mycotic mitigation within the vagina. However, these aforementioned companies primarily base their logic and subsequent assertions upon the fact that there are strains of Lactobacillus which are able to colonize the vagina, and since their strain is a member of the genus Lactobacillus then it should be efficacious. Unfortunately, this supposition or deduction could not be more in error. In a recent study, which examined the various indigenous species and strains of Lactobacilli which colonized the vaginas of 100 healthy women. The results demonstrated that *Lactobacillus acidophilus*was not the most common species of Lactobacillus isolated from the vaginas of these women, but rather the most common strains were found to be: *Lactobacillus jensenii; Lactobacillus gasserii; Lactobacillus salivarius*; and *Lactobacillus casel.*

This aforementioned information, in combination with recent evidence which established that hydrogen peroxide ($H_2O_2$) is a mandatory metabolic by-product for effective bio-augmentation, disproves the previous belief that any strain of Lactobacillus is equally efficacious for use in a suppository-based administration format. Thus, these facts demonstrate the continued need for the development of a product for vaginal supplementation, in combination with an efficacious method of administration, which ameliorates the potential physiological problems associated with the use of both bath products and bathing, in general. More specifically, this product must contain a strain of lactic acid-producing bacteria which possesses such characteristics as: (i) long-term shelf-life and viability; (ii) a rapid growth rate (i.e., a rapid doubling-time); and (iv) a highly efficacious production of lactic acid, so as to produce an acidic environment within the vagina.

(C) Bacterial-Mediated Vaginal Infections

Despite convincing evidence that lower reproductive tract infections possess the ability to migrate to the upper reproductive tract and produce inflammation, stimulate premature labor, and the like, some clinicians still hold to the tenant that lower reproductive tract infections and bacterial vaginosis are merely "markers" of upper reproductive tract infections.

It should be noted that bacterial vaginosis is not truly an microorganism-mediated infection, but instead a microecologic condition in which there are dramatic alterations in the endogenous vaginal microflora. Specifically, bacterial vaginosis involves a reduction in the overall number of lactic acid-producing bacterial strains, with a concomitant multi-log population increase in a characteristic set of microflora including, but not limited to: *Gardnerella vaginalis*, genital anaerobes, and mycoplasmas. Interestingly, these latter microorganisms, along with Streptococci and Coliforms, are the same species as those found in chorioamnionitis.

Additionally, bacterial vaginosis is also associated with increased concentrations of bacterial endotoxin, proteases, mucinases, sialidases, IgA proteases, and phospholipases A2 and C in the lower reproductive tract. Both observational and interventional studies have shown that the presence of bacterial vaginosis in the early stages of pregnancy is associated with pre-term delivery and in later stages of gestation, with miscarriage. These studies suggest that bacterial vaginosis is a direct cause of adverse outcomes in pregnancy, rather than simply being a surrogate marker. Studies suggest that ascending infection or abnormal lower reproductive tract microflora mediate adverse pregnancy outcomes. Similar microbe-host interactions occur in periodontal disease.

Bacterial vaginosis infections can also be mitigated by lactic acid-producing (i.e., probiotic organisms). As previously discussed, the cause-and-effect relationship in bacterial vaginosis is due to the reduction of lactic acid-producing bacterial strains with the resulting multi-log increases of to anaerobic microorganisms including, but not limited to, *Gardnerella vaginalis*. However, the results of a recent, 3900-woman study performed in Denmark demonstrated that absence of bacterial vaginosis was directly associated with sufficient vaginal colonization of aerobic lactic acid-producing organisms. In accord, vaginal supplementation with an effective lactic acid-producing bacterial species will serve to address the imbalance between aerobic lactic acid-producing organisms and the anaerobic species implicated in the etiology of bacterial vaginosis. Such vaginal supplementation may either be utilized prophylactically or therapeutically.

It has now been demonstrated that certain species of lactic acid-producing bacteria can be incorporated into highly alkaline, bath product compositions. These compositions would prove lethal to almost all other species of lactic acid-producing bacteria including, but not limited to: Lactobacillus, Bifidiobacterium, Enterococccus, and various other stains of vegetative cell bacteria.

Administration remains the major problematic issue of vaginal supplementation and, prior to the present invention, there was a long-felt need for an inoculation strategy which made vaginal lactic acid supplementation incidental. The administration of an adequate dose of an effective lactic acid organisms in a bath or shower product would thus address some of the vaginal problems associated with frequent and even occasional bathing, aroma-therapy, sea salt, bath powders, bath gels, bath oils and the like could contain an effective inoculation of lactic acid bacteria for a vaginal application.

The mechanics of this type of administration may be explained in the following manner. After running a warm bath, the woman would add 1–4 ounces of the proposed bath product that contains between approximately $1 \times 10^9$ to $2.5 \times 10^{10}$ vegetative bacterial cells (or spores, depending on the specific bacterial strain which is employed) to the water. The woman would sit in the bath, moving her legs to facilitate vaginal inoculation, for a total of approximately 20 minutes. Subsequently, this treatment could be repeated on the third day (e.g., in cases of acute vuvo-vaginal candidaiasis (VVC) or bacterial vaginitis (BV)), or on a "regular basis" (i.e., at-least monthly) in order to promote the continued stability of the vaginal ecology and microflora. In addition, this methodology should also prove useful in promoting general dermal health, as some species of lactic acid-producing bacteria are useful in the promotion of healthy skin.

Other strains of bacteria that can be used in a bath or shower products include, *Bacillus subtilis, Bacillus laterosporus, Bacillus uniflagellatus, Bacillus pumilus, Bacillus sterothermophilus, Bacillus lentus, Bacillus mycoides*, Sporolactobacillus sp. *Bacillus licheniformis* or any other Bacillus species that out-compete pathogens or has been shown to produce metabolic byproducts that inhibit mycotic or bacterial pathogens. Other attributes that would influence the efficacy of a bath or shower product would include the baro-tolerance (i.e., pressure tolerance), halo-tolerance (i.e., alkaline tolerance) and thermo-tolerance (i.e., heat tolerance) of the specific probiotic organism that is used.

| | |
|---|---|
| *Bacillus coagulans* | 250,000,000 spores (approximately 18 mg) |
| Bath salts (sea & mineral salts) | 10 gm |
| Fructo-oligosaccharides (FOS) | 1 gm |
| Micro-crystalline cellulose (MCC) | 5 gm |
| Fragrance | Trace |

Bath products, including granulated or powdered bubble bath, bath crystals, bath salts, bath oils, powders, aerosol microparticulates and the like, for treatment of vaginal Candida abbicans and/or *Candida tropicalis* infections may be produced in a variety of formulations which contain *Bacillus coagulans* vegetative bacterial or (preferably) spores. In a preferred embodiment, in which bubble baths, bath crystals, bath salts, bath oils and the like are placed in bath water, approximately $1 \times 10^9$ *Bacillus coagulans* spores per ml of an oil-based formulation such as mineral oil, laureth-4, quaternium-18, hectorite, and phenylcarbinol. In a typical bath (approximately 30–100 gallons total volume), a total of approximately $5 \times 10^9$ *Bacillus coagulans* spores are utilized. Natural, oil-based formulations, with or without fragrance, containing approximately $1 \times 10^9$ *Bacillus coagulans* spores per ml of an oil which include, but are not limited to, olive oil, grape seed oil, sweet almond oil, geranium oil, grapefruit oil, mandarin oil, peppermint oil, various essential oils (e.g., Rosemary, Lemon, Geranium, Ylang Ylang, Orange, Grapefruit, Fir, Nutmeg, Balsam, Lime, Peppermint, Vanilla, Lavender, Eucalyptus, Almond, Rose, Palmarosa, Olbas, Kukui Nut, Olibanum and the like), as well as other oils, herbs and materials which are well-known for aroma-therapy applications.

In another preferred embodiment, a non-soap emollient cleanser composition includes sodium octoxynol-2 ethane sulfonate solution in water, petrolatum, octoxynol-3, mineral oil or lanolin oil, cocamide MEA, optional fragrance, imidazolidinyl urea, sodium benzoate, tetrasodium EDTA, methylcellulose, adjusted to pH 6.5 to 7.5, approximately $1 \times 10^7$ to $1 \times 10^{10}$ *Bacillus coagulans* spores per gram. Other suitable cleansers include well-known water-, glycerin-, and sodium oleate-based formulations, adjusted to a neutral pH 7.0, and containing approximately about $1 \times 10^7$ to $1 \times 10^{10}$ *Bacillus coagulans* spores per gram. Hard-milled soaps, made by standard methodologies, may also include about $1 \times 10^7$ to $1 \times 10^{10}$ *Bacillus coagulans* spores per gram, due to the fact that the spores can withstand the pressure and heat necessary for soap manufacturing.

In yet another preferred embodiment, for a powder-based composition, approximately about $1 \times 10^9$ *Bacillus coagulans* spores per gm of talc, powdered oatmeal, cornstarch or similar powdered substance are used.

In still another preferred embodiment, a soft, cloth towelette soaked in a solution of water, potassium sorbate, disodium EDTA and containing approximately $1 \times 10^6$ to $1 \times 10^9$ *Bacillus coagulans* spores per towelette may be utilized to clean the external vaginal area. Additional components to the aforementioned formulation may include DMDM hydantoin, isopropyl myristate, methylparaben, polysorbate 60, propylene glycol, propylparaben or sorbitan stearate. The disposable towelette is used to gently wipe the perivaginal area and is then discarded.

In another preferred embodiment, solid vaginal suppositories or inserts containing approximately $1 \times 10^8$ *Bacillus coagulans* per inert are utilized for mucosal treatment of *Candida abbicans* and/or *Candida tropicalis* infections. Such formulations can be made, for example, from a combination of corn starch, lactose, a metal stearate (e.g., magnesium stearate) and povidone. Typically, one to three solid inserts should be used per day while symptoms (e.g., vaginal itch and/or whitish discharge) are detected. Optimally, one insert per day, for a total of three to seven days, preferably at bedtime, is used.

In yet another preferred embodiment, for an aerosol-based delivery of microparticulates, an aerosol spray may be formulated by combining approximately $1 \times 10^6$ to $1 \times 10^{11}$ *Bacillus coagulans* spores per gm of a carrier mixture which is comprised of isopropyl myristate, approximately about 60% (w/w) SD alcohol 40-B, and isobutane as the propellant. A non-aerosol, manual pump spray containing approximately $1 \times 10^5$ to $1 \times 10^{11}$ *Bacillus coagulans* spores per gm of a neutral aqueous solution may also be utilized. A suitable spray formulation includes alcohol, glycerin, purified water and methylparaben, in addition to the *Bacillus coagulans* probiotic microorganism.

It should also be noted that while the mitigation of yeast infections is the primary vaginal-based utilization of *Bacillus coagulans* therapeutic compositions, these compositions have also been demonstrated to be highly effective in the treatment of non-pathogenic, non-specific dermatitis. Immersion in the therapeutic bathing compositions of the present invention allow the establishment of the probiotic *Bacillus coagulans* on the skin or mucosal membranes, which tends to mitigate dermatitis of unknown etiology.

7.7 Prevention and/or Treatment of Opportunistic Skin Infections

Opportunistic skin infections with Pseudomonas and or Staphylococcus species (i.e., typically *Pseudomonas aeruginosa, Staphylococcus epidermidus, Staphylococcus aureus*, and the like) commonly occur concomitantly with skin allergies (e.g., allergic reactions to plant irritants such as poison ivy), bed sores, diabetic lesions or other types of skin lesions. Probiotic formulations containing *Bacillus coagulans* spores (i.e., approximately $1 \times 10^5$ to $1 \times 10^{10}$/ml depending on the specific formulation and application) and/ or supernatant or filtrate containing extracellular bacteriocins produced by *Bacillus coagulans* or *Pseudomonas lindbergii* strains are highly useful in the prevention or treatment of opportunistic skin pathogens. Additionally, probiotic *Bacillus coagulans* formulations are useful in the prevention of infection with Meticillin-resistant *Staphylococcus aureus* (MRSA), particularly following injury or invasive surgical procedures. A water-in-oil or oil-in-water emulsion, cream, lotion, powder, aerosol powder, or aerosol spray containing approximately $1 \times 10^6$ to $1 \times 10^{10}$ *Bacillus coagulans* spores/ml is used. Various suitable carriers have been previously described herein, and others are well-known within the art.

In the practice of this embodiment of the present invention, the skin is initially cleaned with soap and water and dried thoroughly. The *Bacillus coagulans*-containing therapeutic composition is then applied to the skin, ensuring that the composition is applied to the areas between the toes, under the breasts, under the arms, or any other areas where the skin may become moist or exhibit frictional chafing or abrasion.

In addition to treating the skin topically with an emulsion, cream, lotion, powder, aerosol powder, or aerosol spray containing *Bacillus coagulans* probiotic, the skin may be cleansed with a probiotic formulation such as described herein.

7.8 Treatment of Tineal Fungal Infections

Ringworm (tinea versicolor) is caused by localized infections of the skin of the trunk and neck by dermatophyte fungus which colonizes the outer layer of the skin resulting in generally circular patches of white, brown or pink flaking skin that are often itchy. Once ringworm is detected, the affected area and a surrounding approximately 1 to 10 cm$^2$ area is treated twice daily with a cream or lotion containing 10% by weight *Bacillus coagulans* spores. Suitable carriers are described herein, preferably containing approximately $1 \times 10^5$ to $1 \times 10^{10}$ *Bacillus coagulans* spores/ml of carrier.

For treatment of the related disorder, tinea cruris (i.e., "jock itch"), a powder containing approximately $1 \times 10^7$ to $1 \times 10^9$ *Bacillus coagulans* spores/ml of colloidal silicon dioxide, isopropyl myristate, talc and optional fragrance is applied to the groin area to provide relief of itching, chafing, burning rash and irritation. Treatment is twice daily, generally after bathing and at bedtime, until symptoms are no longer detected.

Clothing, particularly underclothes and nightclothes that come in contact with the trunk and neck are sprayed with an aerosol containing about 1% to about 20% *Bacillus coagulans* active agent in a suitable carrier such as described herein, so as to ameliorate the spread of the infection to additional areas of the body.

7.9 Treatment of Bacterial and Fungal Infections of the Dermis and Cuticle

As previously discussed, various lactic acid-producing bacteria (e.g., *Bacillus coagulans* and *Pseudomonas lindbergii*) have been shown to produce extracellular products that are anti-fungal in nature although all of the products that have come from these bacteria are a result of the purification of a specific active analog such as a protein, carbohydrate or organic molecule to form a new anti-fungal compound. It has been suggested that the use of a single active agent contributes to resistant species of pathogenic fungi and as a result new generations of anti-fungal compounds must be discovered in order to control these new developing species. However, the use of a bacterial supernatant in its crude or in a semi-refined state my be more effective in topical applications and may, in fact, decrease the rate of anti-fungal resistance by providing a more complex killing mechanism that is more difficult to overcome than a single chemical agent or analog.

The use of Emu oil as a "carrier" in the therapeutic compositions of the present invention markedly enhances efficacy in the prevention and/or therapeutic treatment of fungal or bacterial infections of the dermis and cuticle in both humans and animals. These therapeutic compositions are comprised of the fermentation products of specific bacterial strains and, optionally, a commercially available antibiotic or anti-fungal agent in combination with an effective amount of Emu oil in a pharmaceutically acceptable cater suitable for administration to the dermal and/or cuticular membranes of a human or animal.

In various embodiments of the present invention, the final form of the therapeutic composition may include, but is not limited to: a stabilized gel, a lotion, a cream, a semi-solid roll-on stick, a fluid, an aerosol, a spray powder, or an emulsion.

The overall efficacy of the therapeutic compositions of the present invention is relative to the concentration of Emu oil which is utilized in the formulation. Specifically, it has been observed that higher percentages of Emu oil is more effective than lower percentages. Not to be bound by any efficacious percentage, the range of Emu oil used in a topical therapeutic composition of the present invention ranges from approximately 0.5% to 99.9%, with a more preferable range being between approximately 10% to 75%, and the most preferable range being between approximately 25% to 60%. The 0.5% to 99.9% ultimate effective range for Emu oil concentration is due to the very small concentrations of anti-microbial compounds which are typically used in the therapeutic compositions of the present invention. For example, in a dermal application, the anti-fungal agent, Miconazole Nitrate, generally comprises only 2% of the total formulation. The following are examples of therapeutic compositions which have been demonstrated to be effective in the mitigation of bacterial and mycotic diseases of the dermis and cuticle.

| Therapeutic Composition No. 1 | |
|---|---|
| Miconazole Nitrate, Fluconazole, Tolnaftate, Ketoconazole or Intraconazole | 2% |
| Emu oil or Fraction Thereof | 90% |
| Emulsifier | 5% |
| Fragrance | 3% |
| Therapeutic Composition No. 2 | |
| Quaternary Ammonium Chloride, Iodine, Alcohol or Phenolic Compounds | 10% |
| Emu Oil or Fraction Thereof | 80% |
| Emulsifier | 7% |
| Fragrance | 3% |
| Therapeutic Composition No. 3 | |
| Bacterial Supernatant Composition Fermentation Products | 50% |
| Emu Oil or Fraction Thereof | 40% |
| Emulsifier | 7% |
| Fragrance | 3% |
| Therapeutic Composition No. 4 | |
| Bacterial Supernatant Composition Fermentation Products | 50% |
| Emu Oil or Fraction Thereof | 25% |
| Lavender Oil | 2% |
| Hydrosperse Oil | 20% |
| Emulsifying Agents | 3% |

As previously discussed, these aforementioned therapeutic compositions of the present invention may also be utilized in combination with other anti-fungal agents, including, but not limited to: Fluconazole, Intraconazole, Ketoconazole, Tolnaftate, Lamasil, Quaternary Ammonium Chlorides, Phenolics, Iodiphers, and the like. In addition, various other materials (e.g., Titanium oxide) to enhance the whitening of the toe or finger nail may also be used.

In a specific example, a therapeutic composition of the present invention, containing bacterial supernatant derived from *Bacillus coagulans*, was used to mitigate the human fungal infection, Onychomycosis. One ml of the aforementioned therapeutic composition was applied after bathing to each infected nail. Treatment resulted in a change in the green-to-yellow color of the nail within 10 days, in all individuals studied. In addition, within the first 7 days, the detritus under the nail sloughed-off and the thickness of the nail (one of the clinical manifestations of the disease) began to subside. Although the total amount of time which was required to ameliorate this disease varied between each subject, the average time required ranged from one month for superficial infections to six months for more pronounced Onychomycosis. Also, it must be taken into consideration that cosmetic appearance is an aspect of this disease that is independent of the pathology of the nail bed.

In has been demonstrated that the simultaneous anti-fungal action of the bacterial culture supernatant combined with the dermal-penetrating and healing aspects of the Emu oil work in a synergistic manner to ameliorate the fungal infection. It is generally known that Emu oil possess the ability to rehydrate skin cells in a way that promotes the growth of new cells. Similarly, it is quite possible that Emu oil acts in a similar manner in human nail and cuticular tissues.

In other specific examples, a therapeutic composition of the present invention, containing bacterial supernatant derived from *Bacillus coagulans*, was also utilized to treat cases of diaper rash which were complicated with bacterial or fungal infections. Immediate (i.e., approximately 18 hours) relief of the dermal inflammation and redness was achieved, and all of the infections were completely ameliorated within 48 hours. Similar results have been observed in the use of these therapeutic compositions in the treatment of Jock itch (Tinea cruris), Ringworm, Athlete's Foot (Tinea pedis), Scalp infections (Tinea capitis), Beard infections (Tinea barbae), Candidaiasis of the dermis, toe, fingernail and vulva, and other dermal and cuticular diseases.

Various equine hoof diseases (e.g., White Line disease, Hoof Thrush, Drop Sole, and even Clubbed Foot) have also responded to the use of therapeutic compositions of the present invention, containing bacterial supernatant derived from *Bacillus coagulans*, in the same manner as Onychomycosis in humans. In addition, similar to its physiological activity in humans, Emu oil may also function to rehydrate and stimulate new cell growth within animal hooves and other cuticular materials.

7.10 Treatment of Superficial Skin Infections

Superficial infections with Staphylococcus species (e.g., *Staphylococcus aureus* and *Staphylococcus epidermidis*) of a blocked sweat or sebaceous gland cause pustules, boils, abscesses, styes or carbuncles. These superficial skin infections may also be accompanied by a blistering rash (particularly in babies), due to bacterial toxins released by the Staphylococcus species.

A water-in-oil or oil-in-water emulsion, cream, lotion, or gel, containing approximately $1 \times 10^6$ to $1 \times 10^9$ *Bacillus coagulans* spores/ml may be used. An exemplary topical gel is prepared by mixing together equal volumes of propylene glycol and water, 1% by weight hydroxypropyl cellulose (MW of 100,000 to 1,000,000 Daltons) and lyophilized *Bacillus coagulans* culture to a final concentration of approximately $1 \times 10^6$ to $1 \times 10^9$ *Bacillus coagulans* spores/ml of the combination, and allowing the stirred mixture to sit for 3 to 5 days to form a gel. Other formulations are also presented herein.

The *Bacillus coagulans*-containing emulsion, cream, lotion, or gel is applied to the area of the skin showing superficial skin infections (e.g., pustules, boils, abscesses, styes or carbuncles) or rash and gently rubbed into the skin and allowed to air-dry. Applications are at-least once per day, and preferably two to three times per day (e.g., morning and night), or after each washing of the infected area for those areas which are washed frequently (e.g., the hands or diaper area). Applications are continued until skin inflammation has subsided and the skin appears normal to the observer. In cases where scab formation has occurred in the infected area, once daily applications are continued until the scabs are no longer present.

7.11 Acne Treatment

For treatment or prevention of acne vulgaris, a cleanser containing *Bacillus coagulans* active ingredient obtained from a supernatant of bacterial culture is applied daily as a skin care product for removing excess dirt and oil and for preventing opportunistic infection of the skin. A suitable cleanser includes bentonite, cocoamphodipropionate, optional fragrance, glycerin, iron oxides, magnesium silicate, sodium borohydride, sodium chloride, sodium cocoate, sodium tallowate, talc, tetrasodium EDTA, titanium dioxide, trisodium EDTA, water and approximately 1% to about 20% (v/v) of an aqueous supernatant or filtrate of a *Bacillus coagulans* culture grown to saturation.

A similar cleanser, particularly for sensitive skin, includes approximately 30% to 50% colloidal oatmeal, suspended in a base of water, glycerin, distearyldimonium chloride, petrolatum, isopropyl palmitate, cetyl alcohol, dimethicone, sodium chloride, adjusted to pH about 7.0, and containing approximately 5% to about 50% (v/v) of an aqueous supernatant or filtrate of a *Bacillus coagulans* culture grown to saturation.

Alternatively, the skin may be cleansed using any well-known cleanser and then a cream containing an active ingredient derived from a *Bacillus coagulans* or *Pseudomonas lindbergii* culture supernatant or filtrate is applied to the skin in a thin film about once every two days to about three times daily as needed. A suitable cream includes approximately 10% to 12% alcohol (v/v), bentonite, optional fragrance, iron oxides, potassium hydroxide, propylene glycol, titanium dioxide, purified water and approximately 0.5% to 60% (v/v) of an aqueous supernatant or filtrate of a *Bacillus coagulans* or *Pseudomonas lindbergii* culture grown to saturation.

The above formulation is suited for treating acne caused by *Propionibacterium acne* and by *Staphylococcus epidermidis*.

7.12 Treatment of Herpes Simplex I & II and Herpes Zoster Infections

Cold sores (generally found within or around the mouth) are caused by the virus Herpes simplex I; whereas similar lesions around the genitals are caused by Herpes simplex II. Herpes simplex viral infections can also cause painful finger or toe swelling (i.e., Herpetic Whitlow). Both types of Herpes simplex lesions or Whitlow can be treated with a cream, lotion or gel ointment containing approximately $1 \times 10^7$ to $1 \times 10^{10}$ *Bacillus coagulans* spores/ml.

For oral cold sores, a soothing emollient lip balm contains allantoin, petrolatum, titanium dioxide at cosmetically acceptable levels, and approximately $1 \times 10^7$ to $1 \times 10^{10}$ *Bacillus coagulans* spores/ml. The lip balm may further include a sunscreen (e.g., padimate O). An alternative emollient lip balm contains the same base ingredients mixed to form an emulsion with approximately 0.5% to 20% (v/v) of an aqueous supernatant or filtrate of a *Bacillus coagulans* culture grown to saturation. The lip balm is then applied to the lips and affected area to form a light film as a prophylactic when prodromal symptoms are felt (e.g., tingling, itching, burning) or when a lesion is visible. The lip balm should be applied as often as required (e.g., every hour when a lesion is present) and generally once per day at bedtime.

For oral cold sores, the *Bacillus coagulans* spores or extracellular agent in culture supernatant or filtrate may be formulated into a semisolid lip balm containing approximately 20% to 40% white petrolatum, wax paraffin, mineral oil, isopropyl lanolate, camphor, lanolin, isopropyl myristate, cetyl alcohol, camuba wax, methylparaben, propylparaben, titanium dioxide and optionally fragrance and coloring agents.

For genital herpes lesions, a cream or ointment is formulated using standard methods as described herein containing approximately $1 \times 10^7$ to $1 \times 10^{10}$ *Bacillus coagulans* spores/ml and/or approximately 0.5% to 20% (v/v) of an aqueous supernatant or filtrate of a *Bacillus coagulans* culture grown to saturation. The cream or ointment is applied at least twice daily as needed.

For lesions caused by Herpes zoster (i.e., shingles) a cream or ointment is formulated using standard methods as described herein containing approximately $1 \times 10^7$ to $1 \times 10^{10}$ *Bacillus coagulans* spores/ml and/or approximately 0.5% to 20% (v/v) of an aqueous supernatant or filtrate of a *Bacillus coagulans* or *Pseudomonas lindbergii* culture grown to saturation. The cream or ointment is applied at least twice daily as needed.

7.13 Ear Drops or Ear Wash Containing *Bacillus coagulans* Spores

For the prevention or treatment of external ear canal infections, an aqueous formulation that includes approximately $1 \times 10^5$ to $1 \times 10^8$ *Bacillus coagulans* spores/ml and/or approximately 0.1% to 15% (v/v) of an aqueous supernatant or filtrate of a *Bacillus coagulans* or *Pseudomonas lindbergii* culture grown to saturation, is utilized. The spores and/or supernatant is added to a sterile aqueous solution containing approximately 5% to 50% glycerin (v/v), approximately 0.1% to 5% propylene glycol (v/v), and sodium stannate or sodium chloride. An alternative formulation includes approximately $1 \times 10^5$ to $1 \times 10^8$ *Bacillus coagulans* spores/ml and/or approximately 0.1% to 15% (v/v) of an aqueous supernatant or filtrate of a *Bacillus coagulans* or *Pseudomonas lindbergii* culture grown to saturation in a sterile aqueous solution of approximately 0.5% to 25% glycerin (v/v), approximately 5% to 10% alcohol (v/v), and polysorbate 20.

To apply the formulation, the user tilts the head sideways and about 3 to 10 drops of the aforementioned ear formulation is added to the ear using a standard dropper applicator, without having the applicator actually enter the external ear canal. The head is kept tilted for several minutes or, alternately, the ear may be lightly plugged with a wad of cotton so as to allow the solution to remain in the ear for up to 15 minutes. Then the head is then tilted, and excess solution is allowed to drain from the ear. Gentle washing with an ear syringe containing warm water may also be utilized to remove the excess formulation. The probiotic solution can be applied occasionally or daily for up to approximately five days in-total. The accompanying instructions indicate that a physician should be consulted if there is drainage, discharge, rash, severe irritation in the ear, or if the patient experiences dizziness.

7.14 Prophylactic or Therapeutic Treatment of Athlete's Foot

For the prevention or therapeutic treatment of athlete's foot (i.e., tineal fungal infection), the feet are washed with soap and water, dried thoroughly and a powder, cream, lotion, ointment or gel, such as those described in the above examples is applied to the entire foot area. Preferably, the formulation includes approximately $1 \times 10^5$ to $1 \times 10^8$ *Bacillus*

*coagulans* spores/ml and/or approximately 0.5% to 20% *Bacillus coagulans* supernatant or filtrate of a *Bacillus coagulans* or *Pseudomonas lindbergii* culture grown to saturation. Daily treatments are continued as needed.

Additionally, athlete's foot may be prevented or treated by using a standard insole insert (e.g., a fabric, fiber or synthetic foam) having sprayed on the surface or impregnated therein with the *Bacillus coagulans* probiotic or extracellular antifungal product. Such treated insoles may be worn daily for up to two to three months, after which they are discarded and replaced with fresh treated insoles.

Equivalents

From the foregoing detailed description of the specific embodiments of the present invention, it should be readily apparent that unique, improved methodologies for the prevention and/or therapeutic treatment of bacterial, fungal, yeast, and viral infections, have been disclosed herein. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For example, the final form (e.g., stabilized gel, cream, emulsification, and the like) which is selected for the therapeutic composition is believed to be a matter of routine for a person of ordinary skill in the art with knowledge of the embodiments described herein.

What is claimed is:

1. A composition comprising a bacterium or spore of a Bacillus species, wherein said composition contains an amount of colony forming units (CFU) of said bacterium or spore which inhibits growth of a bacteria, yeast, fungus or virus on skin or a mucous membrane of a mammal and wherein said composition is in the form of an emulsion, cream, lotion, gel, oil, ointment, semi-solid formulation, or aerosol spray.

2. The composition of claim 1, wherein said composition comprises a *Bacillus coagulans* spore.

3. The composition of claim 1, wherein said composition comprises a *Bacillus coagulans* vegetative cell.

4. The composition of claim, 1 wherein said Bacillus species is selected from the group consisting of *Bacillus subtilis, Bacillus uniflagellatus, Bacillus laterosporus, Bacillus megaterium, Bacillus polymyxa, Bacillus licheniformis, Bacillus pumilus*, and *Bacillus sterothermophilus*.

5. The composition of claim 1, wherein said composition contains approximately $1 \times 10^3$ to $1 \times 10^{12}$ CFU per gram of composition.

6. The composition of claim 1, further comprising a bifidogenic oligosaccharide.

7. The composition of claim 1, further comprising a bifidogenic oligosaccharide, wherein said bifidogenic oligosaccharide is a fructo-oligosaccharide (FOS).

8. The composition of claim 1, further comprising a bifidogenic oligosaccharide, wherein said bifidogenic oligosaccharide is a fructo-oligosaccharide (FOS) in a concentration ranging from approximately 10 milligrams to 1000 milligrams per gram of composition.

9. The composition of claim 1, further comprising a bifidogenic oligosaccharide, wherein said bifidogenic oligosaccharide is a fructo-oligosaccharide (FOS) in a concentration ranging from approximately 100 milligrams to 500 milligrams per gram of composition.

10. A composition comprising an extracellular product of a *Bacillus coagulans* strain, wherein said composition inhibits growth of a dernal pathogen on skin or a mucous membrane of a mammal and wherein said composition is in the form of an emulsion, cream, lotion, gel, oil, ointment, semi-solid roll-on stick, or aerosol spray.

11. The composition of claim 10, wherein said extracellular product is a supernaut or filtrate of a culture of a *Bacillus coagulans* strain.

12. The composition of claim 10, which further comprises approximately 0.5% to approximately 99.9% Emu Oil, by weight.

13. The composition of claim 1, wherein said dermal pathogen is a bacteria, yeast, fungus, or virus.

14. The composition of claim 10, wherein said dermal pathogen is a bacteria, yeast, fungus, or virus.

15. The composition of claim 1, wherein said composition is in the form of an emulsion.

16. The composition of claim 1, wherein said composition is in the form of a cream.

17. The composition of claim 1, wherein said composition is in the form of a lotion.

18. The composition of claim 1, wherein said composition is in the form of a gel.

19. The composition of claim 1, wherein said composition is in the form of an oil.

20. The composition of claim 1, wherein said composition is in the form of an ointment.

21. The composition of claim 1, wherein said composition is in the form of an aerosol spray.

22. The composition of claim 1, wherein said composition is in the form of a semi-solid formulation.

23. The composition of claim 22, wherein said semi-solid formulation is a semi-solid roll-on stick or semi-solid lip balm.

24. The composition of claim 10, wherein said composition is in the form of an emulsion.

25. The composition of claim 10, wherein said composition is in the form of a cream.

26. The composition of claim 10, wherein said composition is in the form of a lotion.

27. The composition of claim 10, wherein said composition is in the form of a gel.

28. The composition of claim 10, wherein said composition is in the form of an oil.

29. The composition of claim 10, wherein said composition is in the form of an ointment.

30. The composition of claim 10, wherein said composition is in the form of an aerosol spray.

31. The composition of claim 10, wherein said composition is in the form of a semi-solid formulation.

32. The composition of claim 31, wherein said semi-solid formulation is a semi-solid roll-on stick or semi-solid lip balm.

* * * * *